(12) United States Patent
Cameron, Sr. et al.

(10) Patent No.: US 6,764,831 B2
(45) Date of Patent: Jul. 20, 2004

(54) METHODS AND COMPOSITIONS FOR PAIN MANAGEMENT

(75) Inventors: Bruce M. Cameron, Sr., 5532 Cedar Creek, Houston, TX (US) 77057; Robert C. Allen, Mt. Pleasant, SC (US)

(73) Assignees: Proteome Sciences, Inc., Houston, TX (US); Bruce M. Cameron, Sr., Houston, TX (US)

(*) Notice: Subject to any disclaimer, the term of this patent is extended or adjusted under 35 U.S.C. 154(b) by 75 days.

(21) Appl. No.: 09/444,459

(22) Filed: Nov. 22, 1999

(65) Prior Publication Data

US 2002/0086343 A1 Jul. 4, 2002

Related U.S. Application Data

(60) Provisional application No. 60/109,504, filed on Nov. 23, 1998, and provisional application No. 60/141,255, filed on Jun. 30, 1999.

(51) Int. Cl.[7] .............................. C12Q 1/46; C12Q 1/00; G01N 33/53
(52) U.S. Cl. .............................. 435/20; 435/4; 435/7.1; 435/7.4; 435/975
(58) Field of Search .............................. 435/20, 4, 7.1, 435/7.4, 975

(56) References Cited

U.S. PATENT DOCUMENTS

| | | | |
|---|---|---|---|
| 3,378,463 A | 4/1968 | Guilbault et al. | 435/4 |
| 3,401,086 A | 9/1968 | Hoffman et al. | 435/4 |
| 3,410,756 A | 11/1968 | Kramer | 435/4 |
| 3,433,712 A | 3/1969 | Gerarde | 435/4 |
| 3,438,866 A | 4/1969 | Penicnak | 435/20 |

(List continued on next page.)

FOREIGN PATENT DOCUMENTS

| | | |
|---|---|---|
| FR | 4732 | 2/1967 |
| WO | 9210760 | 6/1992 |
| WO | 9632648 | 10/1996 |

OTHER PUBLICATIONS

Yang et al, "Anesthesiology", V 88(2), p. 34, (1998) (Abstract Only).*
Simpson, N.E., *Isozymes: Current Topics in Biological Medical Research,* 11 : 37–49 (1983).
Yamamots, Yasumasa, et al., *Ann. Clin. Biochem.,* 27:321–326 (1990).
Ansermino, J.M., et al., *Anaesthesia,* 48 (12): 1097–1100 (1993).
Diver, Richard P., et al., *Anesthesia & Analgesia,* 82: 1933–1935 (1996).
Hood, David D., et al., *J. of Pharmacol. and Exp. Therapeutics,* 282 (1): 86–92 (1997).

*Primary Examiner*—Louise N. Leary
(74) *Attorney, Agent, or Firm*—Baker Botts L.L.P.

(57) ABSTRACT

The present invention provides novel methods and diagnostic kits for the objective measurement of the severity of pain or stress being experienced by a patient with a disorder, diagnosis and treatment for patients suffering from painful disorders, and monitoring the effectiveness of different pain-treatment protocols. Pain-measuring methods comprise collecting a sample from a patient and determining the presence of a pain-associated marker in the sample. Methods for alleviating pain comprise administrating a dose of a therapeutically effective amount of a composition to the patient wherein the dose is determined by the presence of a pain-associated marker in a biological sample obtained from the patient. Compositions for alleviating pain comprise substances that are pain-associated markers or agents that interfere with pain-associated markers, and block or modulate the progression of pain perceived by the patient.

23 Claims, 7 Drawing Sheets

U.S. PATENT DOCUMENTS

| | | | |
|---|---|---|---|
| 3,928,594 A | * 12/1975 | Cook | 435/20 |
| 4,271,310 A | 6/1981 | Watanabe et al. | 560/71 |
| 4,419,445 A | 12/1983 | Kasabara et al. | 435/20 |
| 4,499,185 A | 2/1985 | Skjold et al. | 435/19 |
| 4,565,780 A | 1/1986 | Montonaga et al. | 435/20 |
| 4,596,772 A | 6/1986 | Kamei et al. | 435/20 |
| 4,717,659 A | 1/1988 | Kuroiwa et al. | 435/20 |
| 4,861,713 A | 8/1989 | Kuriowa et al. | 435/20 |
| 4,889,797 A | 12/1989 | Amano et al. | 435/20 |
| 4,983,756 A | 1/1991 | Kuriowa et al. | 435/20 |
| 5,272,061 A | 12/1993 | Hasselberg | 435/20 |

* cited by examiner

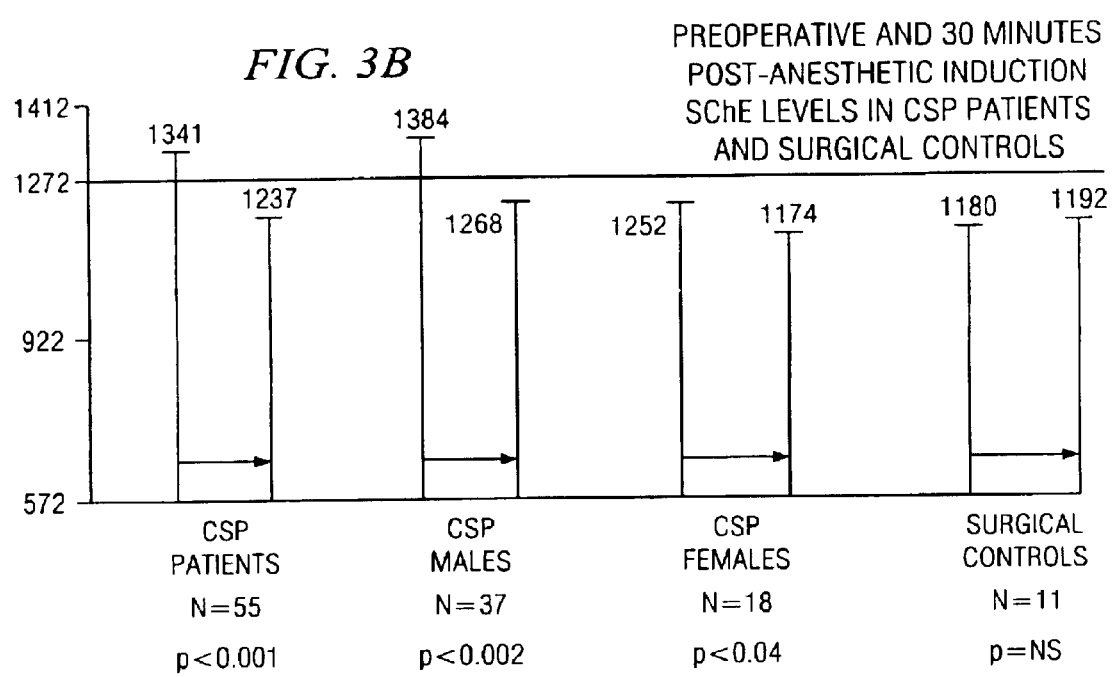
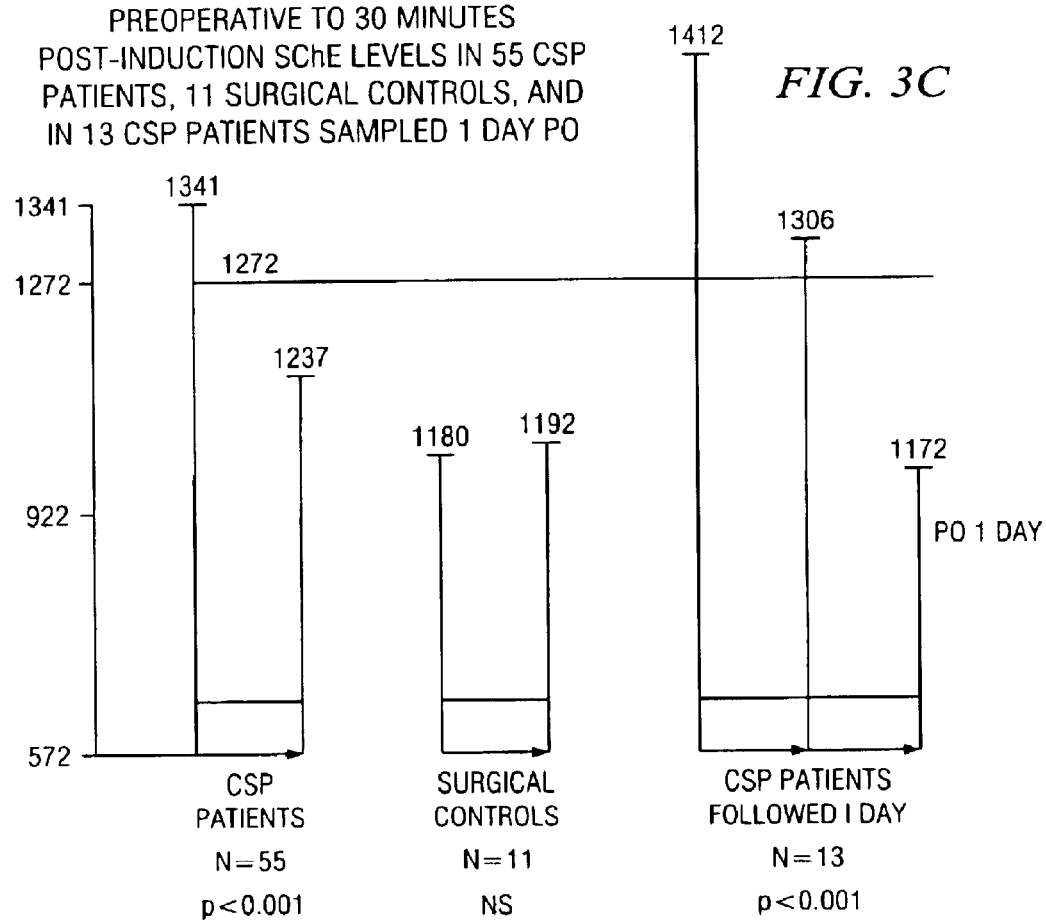

MEANS OF THE PREOPERATIVE AND 30 MINUTES POST-INDUCTION SChE LEVELS OF SEVEN CSP PATIENTS IN WHICH THE LEVEL ROSE > 1SD THE VOLATILITY OF CASE 25 IS ILLUSTRATED

MEAN SChE LEVELS OF NINE DISABLED PATIENTS AND EIGHT CSP PATIENTS

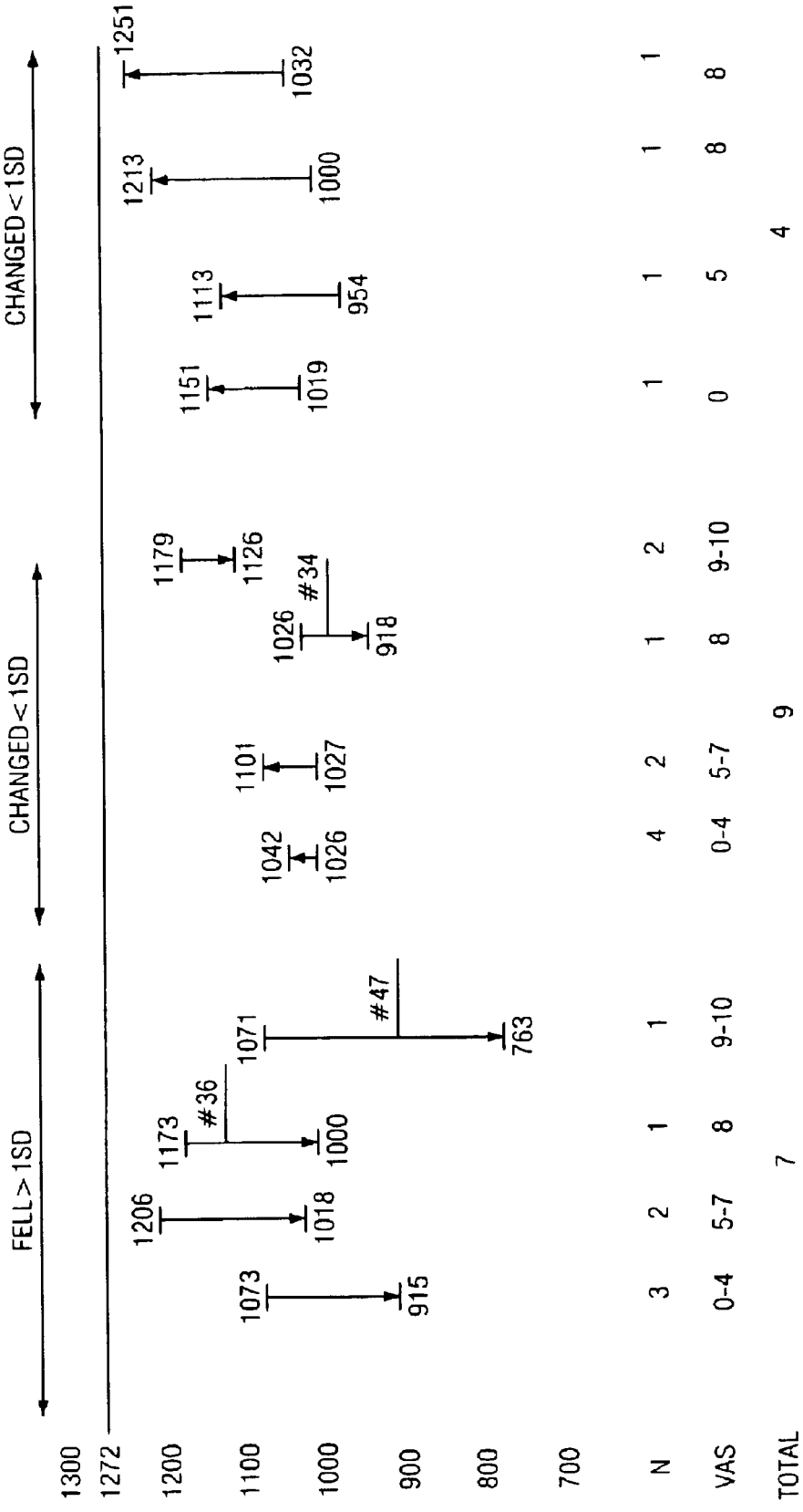

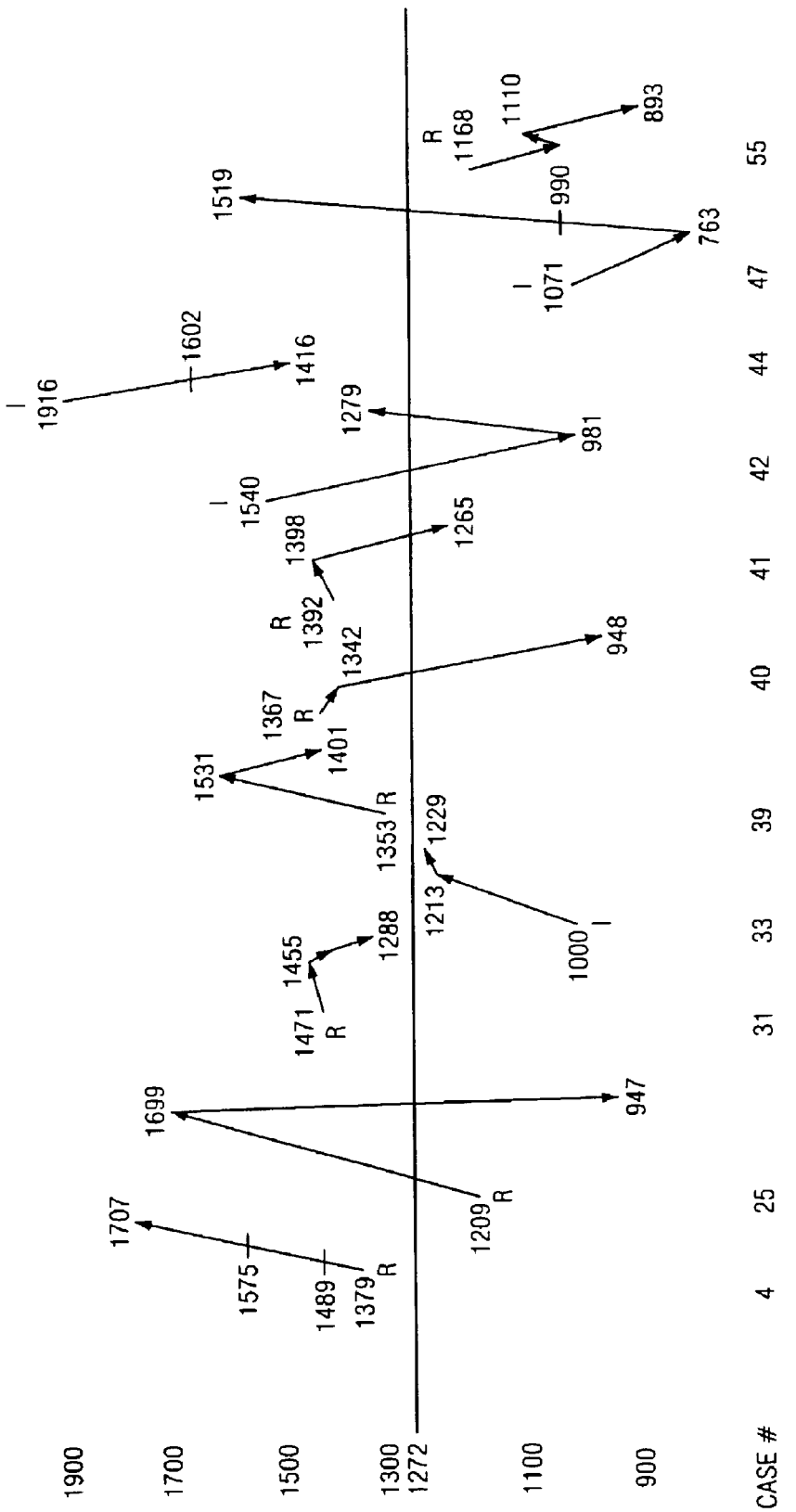

METHODS AND COMPOSITIONS FOR PAIN MANAGEMENT

REFERENCE TO RELATED APPLICATIONS

This application claims priority from U.S. Provisional Patent Application serial No. 60/109,504, filed Nov. 23, 1998, entitled "Objective Assays for Pain Measurement" and U.S. Provisional Patent Application serial No. 60/141,255, filed Jun. 30, 1999, entitled "Therapeutic Methods for Alleviating Pain".

BACKGROUND OF THE INVENTION

1. Field of the Invention

The present invention is directed to methods and diagnostic kits for providing an objective diagnosis of pain or stress experienced by a patient, and to compositions and methods for the alleviation of pain or stress. The invention further relates to reliable diagnostic and treatment tools useful for indicating the efficacy of pain or stress relieving compositions or methods, and the amount of relief provided by conventional treatments.

2. Description of the Background

Pain is a major aliment affecting the population. The analgesic industry and its advertisements are constant reminders of the magnitude of the problem in the population. Of the many types of medical problems involving pain as a major symptom, chronic spinal pain, with its overwhelming presence in the United States and other countries, is one of the most difficult to treat. It is estimated that primary and secondary expenditures associated with chronic spinal pain averages about $100 billion annually in the United States alone. The collateral loss of private and corporate productivity, while never quantitated, is also expected to be significant.

Health care professionals treating patients with chronic spinal pain recognize the limitations of modern diagnostic methods for assessing chronic spinal pain. Current methods for assessment such as, for example, history and physical examination, questionnaires, x-rays, imaging, electromyelograms, imaging techniques and myelograms all suffer from inherent limitation because of their indirect nature. The prevalence of false positive indicators of pain as well as the rise of pain management industries such as clinics, practitioners and alternative treatment centers, give testimony to the problem and the need for objective, accurate laboratory data.

Accurate assessment of a patient's pain is a prerequisite to the successful diagnosis and treatment of chronic spinal pain. Without an objective standard, meaningful comparisons of different treatment protocols will rely on the subjective memories of the patient or the health care worker. Age, stress, infirmity and weakness from long illness may affect the patient's memory. Further, patient self-assessments are of limited value because patients do not always communicate their pain intensity accurately or effectively. Adjectives such as burning, sharp, pressing, stabbing and unbearable are of limited value for comparison between patients. Finally, comparisons of patients with different social, regional, language or cultural background may be extremely difficult because of the choice of adjectives.

In spite of the difficulties in assessment, health care professionals including psychiatrists and psychologists must attempt to adequately assess and manage pain. These attempts require a determination of whether the pain or stress is severe, moderate or mild. A typical diagnosis will also involve a physical examination for accompanying characteristics such as sweating, palpitations, irregular heart beats, fainting sensation, aggravation of pain by deep breathing, pressure, heat or cold. These data, along with any other clinical information, and the patient's own description, is used to determine the most appropriate treatment.

Such pain assessment systems and treatment are empirical and can only provide a rough estimation of the actual amount of pain. Inaccuracies in the ability to prescribe proper amounts of medication result in an inability to provide proper pain treatment. Prescribing too little medication, i.e. under-medication where an inadequate amount of analgesic is used, results in needless suffering, reduced mobility, prolonged hospital stays and delayed recovery. Using too much medication, i.e. over-medication, can result in increased side effects, possible organ damage, allergic reaction, sleepiness, nausea or chemical dependency on analgesics.

Because the diagnosis of pain is difficult and often, if not usually, inaccurate, the ordinary course of treatment for pain will involve multiple office visits. Each visit will involve feedback from the patient, assessment of the efficacy of treatment and periodical changes in the dosage and the type of medications. Frequent office visits lead to an increase in health care cost and lost productivity, at least in part, due to inadequate treatment of pain (i.e. over-medication and under-medication). Further, if the patient's condition changes due to an increase or decrease in severity, a new round of initial medication, office visits, feedback and assessment has to be started to manage the pain. An accurate assessment of pain will result in reduced health care costs, with additional benefits such as earlier patient release, earlier mobilization and reduced reliance on hospital and outpatient medical facilities. Thus, given the significance and magnitude of chronic spinal pain, there is a long felt need for a simple, valid and reliable assay, to be used by health care workers to assess a patient's pain.

Pain is first perceived as a result of the stimulation of specialized nerve endings. The stimulation is transmitted through the nervous system to the brain where the patient perceives the signal as pain. The nervous system, including the brain, comprises about one hundred billion neurons. Each neuron is connected to other neurons in a network. On average, each neuron has, through its axonal and dendritic processes, ten thousand or more connections with other neurons. At the connections of neurons, the cell membranes are not fused but are separated by gaps known as synapses. Signal transduction from neuron to neuron or from neuron to organs (e.g. muscles cells, retina cells, etc.) occur through chemical mediators, referred to as neurotransmitters, that are released into the synapse.

The transmission of a nerve impulse (action potential) along a nerve is electrical and, as such, is measured in millivolts. However, at the synapses, the action potential is transmitted from the pre-synaptic membrane and the post-synaptic membrane of the receiving neuron via protein known as neurotransmitters. The gaps that exist between the neurons and the voltage and current levels of nerve impulses prevent these potentials from passing from one neuron to another neuron directly. Thus, neurotransmitters relay the action potentials between the neurons so nerve impulses can jump this intercellular gap.

When a nerve impulse arrives at the synapse, that impulse is transmitted into a chemical signal via the release of neurotransmitters. The neurotransmitters diffuse rapidly through the intercellular space until it reaches its intended target—the next neuron or muscle cell. There, the chemical neurotransmitter elicits a response in the recipient cell which induces a reaction such as a nerve impulse or a set of intracellular reactions (without necessarily being accompanied by a change of electrical properties). As a result of this process, a signal that began as a nerve impulse is transmitted from one neuron to another and either enhanced, inhibited or blocked.

About fifty neurotransmitters have now been identified. Some, such as glutamate or acetylcholine stimulate the transmission of nerve impulses and are referred to as excitatory; others, such as [Gamma]-aminobutyric acid (GABA), decrease nerve impulse transmission and are called inhibitory.

GABA, glutamate and acetylcholine (ACh) are the major transmitters of the brain. Evidence has confirmed cholinergic involvement in the antinociceptive effect of GABA (Kendall D. A., et al., J. Pharmacol. Exper. Therapeutics, 220(3):482–7, 1982). Additionally, ACh was thought to be involved in nociception with, or in association with, the endorphinergic and serotonergic systems (Schneck H. J. and Rupreht J., Acta Anaesth. Belg. 40(3):219–28, 1989). There is thought to be a close relationship between cholinergic afferents, substance P interneurons and serotonergic receptors (Feuerstein T. J. et al., Naunyn-Schmiedebergs Archives of Pharmacology, 354(5):618–26, 1996).

The descending connections of the midbrain, especially from the hypothalamus and zona incerta, may be some of the components of the neural networks that regulate nociception (Morrell J. I. et al., J. Comp. Neurol., 201(4):589–620, 1981). A descending or local spinal cholinergic system, together with descending serotonergic and noradrenergic systems, has been found to be involved in the centrifugal inhibition of spinal nociceptive transmission (Zhuo M. and Gebhart G. F., Brain Res., 535(1):67–78, 1990). These cells provided cholinergic innervation to the entire brainstem reticular formation. Investigators have found that ascending fibers to the thalamus and descending fibers into the medullary reticular formation are involved in sensory-motor inhibition (Jones B. E., Neuroscience, 40(3):637–56, 1991).

Another chemical, important in transmission of nerve impulses, is the enzyme serum cholinesterase (SChE). SChE, also known as pseudocholinesterase, has been documented to increase when the neuronal activity of the cholinergic system of the brain is activated with pain such as chronic spinal pain. With this activation, ACh is spilled into extracellular spaces (Kurokawa M. et al., Neuroscience Left., 209(3):181–4, 1996), where it is degraded by SChE (Cooper J. R. et al., *The Biological Basis of Neuropharmacology*. New York: Oxford University Press, 27–216, 1996; Guyton A. C., *Basic Neuroscience, In: Anatomy and Physiology*, Philadelphia: W. B. Saunders Co., 1987). ACh is the only neurotransmitter hydrolyzed prior to uptake into the presynaptic neuron for resynthesis; all others are taken up without degradation (Chen D. and Lee K. H., Biochem. Pharmacol., 49(11):1623–31, 1995; Ghelardini C. et al., Life Sc. 58(25):2297–309, 1996). However, some excess, intact ACh is found in the extracellular space. This excess ACh is thought to be degraded by SChE (Cooper J. R. et al., 7 *The Biological Basis of Neuropharmacology*. New York: Oxford University Press, 27–216, 1996; Kurosawa M. et al., Neurochem. Int. 21(3):423–7, 1992; Scali C. et al., Euro. J. Pharm.; 325(2–3):173–80, 1997). Other investigators report that ACh is degraded primarily in the extracellular space (Todorov L. D. et al., Nature 387:76–9, 1997; Ishii Y. et al., Japanese J. Pharm., 66(3):289–93, 1994). Stimulation of sectioned sciatic nerves in cats also produced a prompt increase of cholinesterase in the cerebral spinal fluid (CSF) (Vogt M. et al., Neuroscience 12:979–995, 1984).

It was reported that noxious stimulation can increase ACh in the cerebral cortex (Mitchell J. F. J. Physiol., 165:98–116, 1963; Phillis J. W. Brain Res., 7:378–9, 1968). However, there are also reports that pain produced an intense neuronal activity (INA) throughout the CNS, and diffuse CNS neuronal activity with pain (Dixon C. E. et al., Neuroscience Lett., 198(2):111–4, 1995; Dubovy P. et al., Cellular Molecular Biol., 36(1):23–40, 1990; Eisenach J. C. et al., Anes. Anal., 82(3):621–6, 1996).

The cholinergic system is part of this neuronal activity. The neurotransmitter ACh was first identified in 1900, and its properties noted in 1925. The ACh system was found widely disposed throughout the CNS and shown to have properties for processing pain. In the synaptic cleft, ACh is degraded into choline and acetate by cholinesterase present in the synaptic area bound to local collagen and glycosaminoglycans. The ACh that is not degraded spills into the extra-cellular space and is degraded by SChE (Cuadra G. and Giacobini E., J. Pharm. Experimental Therapeutics, 275(1):228–36, 1995, Messamore E. et al., Neuropharm. 32(8):745–50, 1993). Injection of physostigmine and heptylphysostigmine into rats appears to result in an elevation of the ACh level in the extracellular space (Cuadra G. and Giacobini E., J. Pharm. Exper. Therapeutics, 275(1):228–36, 1995; Cuadra G. et al., J. Pharm. Exper. Therapeutics, 270(1):277–84, 1994). Further, neostigmine has been shown to inhibit cholinesterase and to produce an extracellular ACh level which is above detection limit (Messamore E. et al., Neuropharm.; 32(8):745–50, 1993). Anti-cholinesterase drugs can increase the extracellular levels of ACh and decrease the level of cholinesterase (Ishii Y. et al., Japanese J. Pharm., 66(3):289–93, 1994). With a turnover time of 150 microseconds, equivalent to hydrolyzing five thousand molecules of ACh per second, cholinesterase ranks as one of the most efficient enzymes (Cooper J. R. et al., The Biological Basis of Neuropharmacology. New York: Oxford University Press, 27–216, 1996).

Stimulation of the nucleus basalis of Meyert increases both cortical blood flow and a release of ACh in the cortex in rats. This stimulation produces a measurable, increase in the extra-cellular ACh (Kurokawa M. et al., Neuroscience Lett., 209(3):181–4, 1996). Further, a stimulus to the paws of anesthetized rats produces a significant ($p<0.05$) elevation of extracellular ACh (Kurosawa M. et al., Neurochem. Int., 21(3):423–7, 1992).

A monitoring system, a periventricular structure, was found in animals to consist of cholinergic receptors in the vessels of the anterior and intermediate pituitary lobes that are known as blood ACh reading bodies (BARBS) (Caffe A. R., Histol. Histopathol., 11 (2):537–51, 1996). When ACh is injected into the brachial artery of humans, extreme pain was produced (Cooper J. R. et al., The Biological Basis of Neuropharmacology. New York: Oxford University Press, 27–216, 1996; Hata T. et al., Japanese J. Pharm. 41(4) :475–85, 1986). BARBS may regulate homeostasis of ACh in the blood of the brain. For example, when ACh is high, as would occur with the neuronal activity caused by CSP, BARBS may signal the liver which responds with a homeostatic response to remove excess ACh from plasma by increasing SChE.

Previously, afflictions such as, for example, disease of the kidney or liver, have been shown to correlate with an alteration in the level of cholinesterase. Thus, numerous methods directed to assaying cholinesterase and serum cholinesterase exist (U.S. Pat. Nos. 3,378,463; 3,433,712; 4,271,310; 4,596,772; 4,861,713 and 5,272,061). None of these, however, disclose methods for determining the level of pain perceived by a patient by measuring cholinesterase levels.

SUMMARY OF THE INVENTION

The present invention overcomes many of the problems, limitations and disadvantages associated with current strategies and designs and provides novel methods and diagnostic assays for the detection and quantitation of pain and stress.

One embodiment of the invention is directed to methods of diagnosing the intensity of pain perceived by a patient comprising determining the amount of a marker in a biological sample obtained from said patient wherein said marker correlates with the perception of pain. These methods are useful for quantitating and monitoring either acute or chronic pain and especially useful for the detection and measurement of chronic spinal pain. Biological samples in which a marker can be detected include blood, serum, lymph fluid, tears, semen, intracellular fluid, interstitial fluid, cerebrospinal fluid, urine, sweat and saliva. Detection may comprise determination of the amount of marker in the sample or marker may be isolated and purified. Isolation can be performed by electrophoretic separation such as polyacrylamide gel electrophoresis.

Another embodiment of the invention is directed to methods for determining the intensity of a pain perceived by a patient. These methods comprise collecting a biological sample from the patient and that may contain a marker whose presence, absence or quantity correlates with the intensity of pain perceived by a patient. The amount of marker in the sample is determined using, for example, an ELISA or other detection or quantitation tool and the intensity of pain perceived by the patient objectively determined based on the amount of marker in the sample. Preferably the marker is a neurotransmitter or a metabolic product of a neurotransmitter such as cholinesterase. The relative amount of cholinesterase in the sample is determined and compared to the amount of cholinesterase in a control sample obtained from a subject without pain. The patient and the control subject may be the same person or different people or groups of individuals.

Another embodiment of the invention is directed to methods for determining the intensity of a pain perceived by a patient by determining the amount of cholinesterase in a sample of body fluid obtained from the patient. Such methods are particularly useful for the detection and quantitation of chronic pain such as chronic spinal pain.

Another embodiment of the invention is directed to methods for identifying a marker that correlates with the intensity of a pain perceived by a patient. These methods comprise collecting a serum sample from the patient and separating the components of the sample from each other by gel electrophoresis. The gel is reacted with a diazonium salt and a substrate for a period of time to form a detectable band comprising an insoluble diazonium complex. The size and location of the detectable band that correlates with the patient's perception of pain can be quickly and easily identified.

Another embodiment of the invention is directed to methods for determining the efficacy of a treatment for pain. These methods comprise determining a first severity of pain in the patient by determining the amount of a marker in a first biological sample obtained from the patient. After the desired treatment is administered to the patient, a second severity of pain in the patient is determined by measuring the amount of marker in a second biological sample obtained from the treated patient. By comparing the first severity of pain to the second severity of pain, based on the relative amounts of marker in the samples, an objective assessment of the effectiveness of the treatment can be determined. Such methods may also be used for target validation in determining the most appropriate target in the overall treatment of pain perceived by the patient.

Another embodiment of the invention is directed to diagnostic kits for determining the severity of pain in a patient. These kits comprise at least one agent that reacts with a marker whose presence in a biological sample correlates with the perception pain in a patient from whom the sample is obtained. For example, kits may contain a plurality of antibodies that are specifically reactive against or bind specially to the marker. These antibodies may be polyclonal, monoclonal or simply antibody fragments. The agents may also be substrates when the marker is an enzyme. Substrates that can be used for a cholinesterase marker include ACh and ACh analogs, a protein cleavable by cholinesterase, 4-chloro-2-methylaniline and combinations of these substances.

Another embodiment of the invention is directed to pharmaceutical compositions comprising a therapeuticaly effective amount of a pain-associated marker or an agent that interferes with the perception of pain by the patient. Preferably, the composition selectively inhibits the pain-associated activity of ACh. In a preferred embodiment the pain-associated marker is cholinesterase. Administration of compositions directly or indirectly affect the activity of ACh and interfere with the generation or progression of pain being perceived by the patient.

Another embodiment of the invention is directed to methods of treating a pain being experienced by a patient. Methods of the invention comprise administration of a composition to the patient as determined by the presence of a pain-associated marker in a biological sample obtained from the patient. Compositions may contain new or conventional pharmaceuticals of an amount and type as determined from the presence and quantity of a pain-associated marker in a biological sample obtained from the patient.

Other embodiments and advantages of the invention are set forth, in part, in the description which follows and, in part, will be obvious from this description and may be learned from the practice of the invention.

DESCRIPTION OF THE DRAWINGS

FIG. 3(B) Preoperative and post-anesthetic induction SChE levels in CSP patients and surgical controls.

FIG. 3(C) Preoperative to post-induction SChE levels in CSP patients and surgical controls.

FIG. 7 Preoperative to post-induction SChE levels in CSP patients with preoperative levels less than 1272.

FIG. 8 Pre to intraoperative SChE levels in CSP cases.

DETAILED DESCRIPTION OF THE INVENTION

Figure 1:
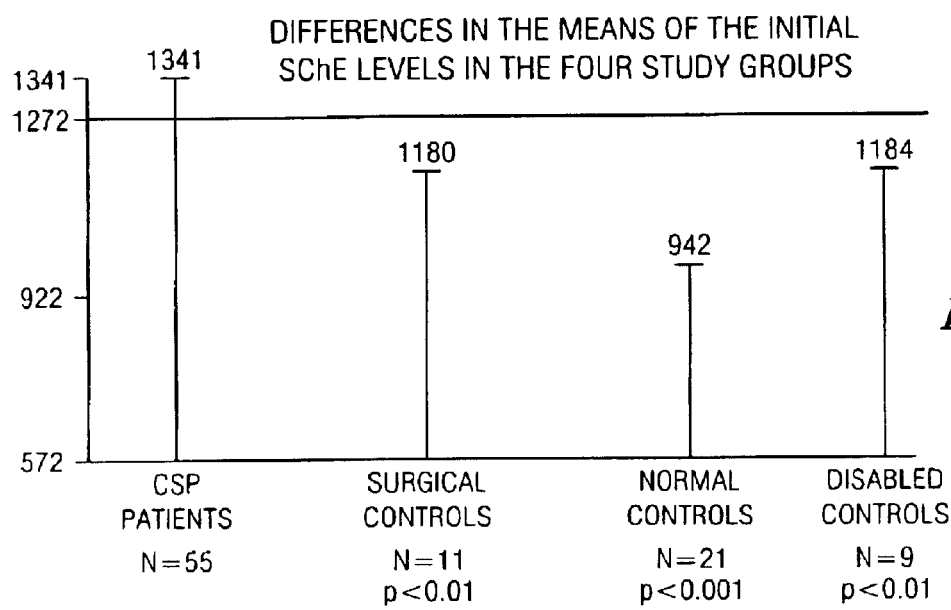
FIG. 1 Differences in the means of initial SChE levels in four study groups.

As embodied and broadly described herein, the present invention is directed to reliable and reproducible methods and diagnostic assays that provide an objective determination of pain or stress experienced by a patient.

Pain, which affects the entire population at one time or another, can be either or both chronic and acute. Although pain is most often a symptom of a disorder, it can also be a disorder in and of itself. Spinal injuries are most closely associated with chronic pain, but other disorders, such as systemic infections, arthritis and cancer, are also causes of chronic pain. The treatment of pain, including chronic pain, typically involves the administration of analgesic medication. Analgesics relieve pain by altering a patient's perception of nociceptive stimuli without producing anesthesia or loss of consciousness. Although there have been some efforts to find objective indicators for pain, those efforts are hampered by the problems of genetic variability and variations due to an individual's perception of pain. One study provided an objective diagnostic test for peripheral nerve damage that causes chronic spinal pain. U.S. Pat. No. 5,364,793 and U.S. Pat. No. 5,583,201, both of which are specifically incorporated by reference, describe an acute phase protein, apolipoprotein E, originally thought to correlate with damage caused by peripheral nerve damage which caused chronic spinal pain (Vanderputten D. M. et al., Applied Theoretical Electrophoresis, 3:247–252, 1993). it was later found that this correlation was not statistically significant for clinical use. Thus, it is still very difficult to accurately and objectively assess another person's pain level. Consequently, determining the correct medication and determining the proper dosage of that medication to treat a patient's pain is equally difficult.

It has been surprisingly discovered that an objective determination of a patient's perception of pain can be achieved by quantitating a biological marker that closely correlates with the intensity of that pain. By determining the level of that marker in a sample obtained from the patient, an accurate assessment of pain intensity can be made and, thereby, appropriate treatment initiated. In addition, the problems of pain type and intensity experienced by a single patient have been overcome, in part, by following a single individual over time. In this way, the perception of pain was entirely individualized and consistent for each person, negating complications associated with genetic variability. Thus, and for the first time, a correlation between a marker and pain is accurately and reproducibly realized.

Pain markers may also be useful in a similar context for the objective detection and assessment of stress. Stress has long been known to be associated with the autonomic nervous system. This system could also provide objective markers for the detection and assessment of stress which would be useful to health care providers such as psychiatrists and psychologists to both the objective assessment of a patient's condition as well as the ultimate treatment administered. Such markers may also be useful for the detection of the perception of supratentorial or phantom pain. Accordingly, pain markers, as used herein, should be considered potentially useful as stress markers and stress markers potentially useful as pain markers. In a similar fashion as the cholinergic system is considered a source of potential pain markers, the autonomic nervous system, including associated neurotransmitters and enzymes, is a repository of such stress markers.

One embodiment of the invention is the identification of markers that correlate with the perception of pain. These markers are preferably neurotransmitters that are directly involved with the sensation of pain such as, for example, amino acid transmitters (e.g. glutamic acid, aspartic acid, cysteic acid, homocysteic acid, GABA, glycine, taurine, beta alanine), ACh, the catecholamines (e.g. norepinephrine, epinephrine, dopamine), serotonin, histamine, the neuroactive peptides (e.g. vasopressin, oxytocin, somatostatin, cholecystokinin, VIP-related peptides, substance P, enkephalin, NYP, neurotensin, TRH, enkephalin, CCK, dynorphin, the tachykinin peptides, the pancreatic polypeptides, opioid peptides, calcitonin gene-related peptide, corticotropin-releasing factor), and combinations thereof. Pain markers may also be intermediate metabolic products of neurotransmitters such as, for example, products produced for anabolism of neurotransmitters or products produced by catabolism of neurotransmitters and, preferably enzymes involved in the sensation of pain such as, for example, SChE. Of course, markers nay be combinations and mixtures of any of the foregoing. The successful correlation of the presence, absence or absolute quantity (or relative quantity at a particular location) of a particular marker or combination of markers may sometimes be related to the location from which a biological sample is obtained from the patient. For example, certain markers may be undetectable, or the quantity may not vary in proportion to the pain experienced from some locations, but not others. Accordingly, sampling from some locations within the body may indicate a lack of correlation with the sensation of pain. However, those same markers may correlate when sampled from other locations such as locations which are involved with the sensation of pain, either directly or indirectly. One such example is the correlation between SChE and its presence in blood.

The pain that is actually measured for severity may be either or both, chronic or acute pain. Typical causes of acute pain include, for example, invasive and surgical procedures on a patient, stress, infections, lacerations, violent injuries and combinations thereof. Chronic pain is typically associated with spinal injuries and disorders such as herniated or ruptured discs and chronic back syndrome. Chronic pain can also be caused by conditions such as cancer, systemic infections, stress, arthritis and combinations of these disorders. Chronic back pain can be divided into upper cervical or neck pain, thoracic pain and lower back pain, any of which can be a radiating pain that may manifest itself in other areas of the body.

To identify marks associated with pain, and also stress, a biological sample, preferably a serum sample, is obtained from the patient. Peptides and proteins within the serum are, for example, separated by electrophoreses in a polymeric or other type of gel so as to sufficiently separate and distinguish potential markers. Gel electrophoresis as is well known in the art and encompasses a number of techniques. One dimensional non-denaturing electrophoresis separates proteins based on the combined effects of charge and apparent size. It may also be used to separate proteins based on their isoelectric points in an isoelectric focus medium. Two-dimensional gel electrophoresis separates proteins based on isoelectric point and size. Two-dimensional electrophoresis may be performed, for example, where separation on a first dimension is based on isoelectric point (i.e. isoelectric focusing) and where separation on a second dimension is based on size (i.e. denaturing gel electrophoresis). Any electrophoresis technique known to the art, such as stacked gels, gradient gels, pulsed electrophoresis, orthogonal pulsed electrophoresis may be used. Other methods for separating proteins, such as, for example, thin layer chromatography, column chromatography and the like may also be used. For example, the serum may be separated by capillary electrophoresis and each resultant fraction may be analyzed directly. Alternatively, each capillary electrophoresis fraction may be immobilized on an absorbent material such as a gel or paper and reacted and analyzed while immobilized.

To identify potential markers for pain within the polymeric gel, the gel is reacted with a diazonium salt and a substrate for a period of time to form an insoluble diazonium complex band. After the formation of the diazonium complex band, the gel is treated with a stopping reagent and the amount of diazonium complex measured. One preferred diazonium salt is FAST Red TR (4-chloro-2-methylaniline, Sigma, St. Louis Mo.). Other diazonium salts that may be used include. One preferred stopping reagent is acetic acid. Other stopping agents that may be used include other carboxylate acids such as formic acid, acetic acid and citric acid. The amount of stopping agent used will be a function of the strength of the stopping agent and the duration of the treatment. The strength of the stopping agent may be affected by other factors such as, for example, the temperature of the reaction, the density of the polymeric gel and the frequency of agitation. If acetic acid is used as the active ingredient in a stopping agent, the stopping agent may comprise between 2% to 50% acetic acid, preferably between 5% and 25% acetic acid and most preferably about 10% acetic acid. Bands whose presence, absence or intensity that correlate with the pain are easily visually identified.

The amount of enzymatic activity or simply the amount of protein in the band may be determined by analyzing the amount of immobilized product in the polymeric gels. While any method for determining the amount of immobilized product may be used, one preferred method is optical analysis. Examples of optical analysis include visual comparison of samples with known controls, scanning for optical density at various wavelengths (i.e. densitometry), scanning for optical density with white light. The polymeric gel may be dried before optical analysis. Polymeric gel drying is a well known technique and may involve, for example, fixing the gel to a flat substrate such as glass, paper or polymer sheets, and removing liquids from the gel by heat, vacuum, or a current of dry gas or air. The amount of enzymatic activity or the amount of protein may be quantitated manually or by computer.

Another embodiment of the invention is directed to a method for determining the intensity of pain perceived by a patient by quantitating a pain marker (i.e. a biological marker that correlates with the perception of pain or stress), in a sample obtained from the patient during the painful episode. The sample may be a sample of tissue or fluid, and is preferably a bodily fluid. Bodily fluid samples include, for example, cerebrospinal fluid, blood, plasma, serum, saliva, lymph fluids, tears, sinus, sweat, urine or combinations of such samples. The sample may be used immediately or stored such as, for example, by refrigeration, freezing or another technique that preserves the marker for later analysis. The amount of markers in the preserved or fresh sample is than quantitated and compared with a standard. The standard may be individualized for a patient, a patient population such as race, gender or ethnic background, or simply a random or selected group of individuals. Upon comparison, the quantity of markers in the sample will correlate with an objective level of pain intensity being experienced by the patient at the time of sampling. From this information, the patient can be administered the correct amount and type of medication to treat that pain which may be no medicine at all.

To assist in carrying out an assay to measure pain, using the methods and kits of this invention, standard enzyme levels can be recorded using normal controls. A normal control is a matched subject who does not suffer the painful disorder exhibited by the patient. A matched subject is ideally the patient himself or herself during an episode where he or she is not presently experiencing the pain, or a person with the same genotype and phenotype (e.g. age, sex, physical condition, etc.) as the patient—an identical twin that does not suffer from the disorder. Another preferred matched subject is the patient himself before he suffers from the painful or stressful disorder. When an ideal normal control is not available, the normal control may be produced by sampling and pooling data from subjects that are closely matched to the patient.

Another embodiment of the invention is directed to a database, preferably a computer database, of standard enzyme levels of subjects with and without pain and stress. The database can be organized to provide general breakdowns by patient characteristics, by pain indicator measured, by stress indicator measured or by any other identifiable characteristic. The enzyme profile of a patient may be compared with this database to determine the relative amount of pain perceived by the patient as compared to other known pain and stress profiles.

Another embodiment of the invention is directed to a method for determining the intensity of stress perceived by a patient by quantitating a stress marker (i.e. a biological marker that correlates with the perception of stress), in a sample obtained from the patient. Stress is a physical, mental, physiological, physiopathological, or emotional disruptive or upsetting condition which occurs in response to a physical disorder, an adverse external influence, and trauma. Trauma include events such surgery, accidental injury or illness from a disorder. Stress is capable of affecting physical health, usually characterized by increased heart rate, a rise in blood pressure, muscular tension, irritability and depression. Stress is also capable of disturbing the biochemical and biophysical homeostasis of a patient. The present invention also provides diagnostic kits and methods for determining and characterizing the stress level in a patient. Diagnostic kits of the invention comprise one or more substrate capable of interacting with one or more enzyme whose presence in the body fluid indicates stress.

Another embodiment of the invention is directed to diagnostic kits used to assess or monitor the level of pain being experienced by a patient. Kits comprise agents that interact with one or more of the markers that correlate with pain such as, for example, SChE or metabolic products of SChE. Preferably, agents are antibodies that are reactive against or bind specifically to one or more epitopes of the marker. These antibodies may be polyclonal or monoclonal or portions of antibodies such as portions that bind to the marker. Agents may also be enzymatic substrates such as, for example, when the marker is an enzyme. Reaction of enzyme marker with substrate is detectable through production of a product which be itself be detectable or labeled with a detectable label. For example, kits comprising substrate can be reacted with biological samples containing a cholinesterase, such as SChE. Reaction of the substrate with cholinesterase forms a product. The amount of substrate remaining or the amount of product produced is monitored both before and after contacting the biological sample. Tests may be competitive or non-competitive, both of which are well-known to those of ordinary skill in the art. Either the substrate or the product may be the detectable which allows for quantitation of the amount enzyme in the sample and an estimation of the amount of marker in the patient. The amount of marker in the body, in turn, provides an objective determination of the intensity of pain being perceived by the patient. Markers such as antibodies may be fixed to a solid support and fixed in a fashion to provide a quantitative assessment of the quantity or relative quantity of that marker in the sample. Solid supports that may be used include sticks, wells and other structures composed of plastic or another inert material.

In another embodiment of the invention, kits can be used to accurately determine the effective treatment to be administered to a patient for the amelioration or complete relief of pain being experienced by the patient. This can be critically important when treatment involves an analgesic medication where over medication or under medication of the patient is a serious risk or problem. It is well established that excessive and insufficient dosages of analgesics and also excessive pain produce distractions and can impair performance. Such patients include individuals with disorders and disabilities associated with pain, candidates for surgical procedures and people with responsibilities that involve public safety or who are engaged in hazardous occupations. An objective measurement of pain will allow accurate and quick pain management without any possible side effects of excessive or insufficient analgesics. Many such analgesics whose effects on individuals and groups of individuals can be accurately and quantitatively determined include, for example, aspirin (acetylsalicylic acid), acetaminophen, codeine, morphine, butorphanol, diperone, fenoprofen, fentanyl, banamine and may others including combinations of these medications. Treatments that can be measured using kits of the invention include less conventional modalities such as, for example, pain relieving devices, and even more basic treatments such as, for example, exercise. As an objective determination, the amount of treatment necessary to alleviate or simply reduce the pain being experienced by the patient can be accurately determined and treatment effectively administered. Kits are especially useful for treating seriously ill patients, comatose or other non-responsive patients, infants and animals including, for example, horses, house pets such as dogs and cats, zoo animals such as elephants, zebras, rhinoceros, giraffe, bears, lions and tigers, and nearly every other mammal.

Another embodiment of the invention is directed to a method to determine the efficacy of an analgesic in a patient. In the embodiment, an initial measurement of a marker associated with pain is made using the method of the invention. After a determination of the severity of pain, an analgesic is administered to the patient. After allowing an appropriate of time for the analgesic to take effect, a second pain measurement is made. A comparison between the initial pain measurement and the second pain measurement may be made to determine the effectiveness of the analgesic. In another embodiment, this method can be applied to determine the effectiveness of a modality of a surgical procedure. As is well known to surgeons, there are a variety of surgical options in the treatment of, for example, chronic spinal pain. These options may include surgical intervention using screws and cages secured to bones, implantation of electrical or mechanical devices, or bone grafting. A critical piece of information in choosing the appropriate option is to objectively determine which would provide the greatest relief from the perceived pain and, also, the procedure itself that would induce the least pain and possible the fastest recovery. By determining the amount of pain being perceived at any given time, the surgeon can accurately assess the effectiveness of and discomfort associated with the treatment.

Another embodiment of the invention is directed to a method for determining the severity of a painful disorder, such as, for example, chronic spinal pain, in a patient. In the method, a body fluid, such as blood or serum, is collected from a patient. The body fluid is assayed for a biochemical activity which is indicative of the severity of the painful disorder in the patient. The level of biochemical activity is used to determine the severity of the painful disorder in the patient. The biochemical activity assayed may be a cholinesterase activity such as, for example, SChE. It has been shown that neuronal activity of the cholinergic system of the brain increases when the brain is activated, for example, by chronic spinal pain. With this activation, ACh spills into extracellular spaces where it is degraded by SChE. There are two ChE: one acts in the molecule of the synaptic cleft; and the other is SChE that acts on the ACh spilled into the extracellular space. Unlike most other neurotransmitters, ACh is not reabsorbed, but hydrolyzed. Thus, the spill may produce a demand for SChE and, thus, SChE increases, probably as a signal to the liver. Although some believe that most ACh hydrolysis is in the extracellular space, it is the increased neuronal activity produced by pain that produces a demand for SChE and, therefore, the increased presence of ACh (e.g. in the CNS) and SChE (e.g. in bodily fluids) which makes these biological components objective markers for pain.

To determine the severity of the painful disorder, the biochemical activity may be compared with a known standard or to a control. A control may be a matched subject. A matched subject means a subject that is as close as possible to the patient but who does not suffer from the painful condition. For example, a match subject may be the patient or a person of the same age, sex or physical condition as the patient. Preferably, the matched subject has the same or a similar phenotype (i.e. one or more of the same or similar characteristics of height, weight, age, sex, medical history, etc.) to the patient and may have the same or unrelated aliments. That is, if the patient suffers from diabetes and alcoholism a matched control subject may also suffer from diabetes and alcoholism. A control that is a perfectly matched subject is difficult to find and pooled data from a number of control subjects that are similar to the patient may be used.

Another embodiment of the invention is directed to a composition containing a pain-associated marker that interferes with the progression of or inhibits pain being experienced by a patient. These markers are preferably neurotransmitters that are directly involved with the sensation of pain such as, for example, amino acid transmitters, ACh, the catecholamines, serotonin, histamine, the neuroactive peptides, derivatives of these compounds such as, for example, butyl choline, and combinations thereof. Pain markers may also be intermediate metabolic products of neurotransmitters such as, for example, products produced for anabolism of neurotransmitters or products produced by catabolism of neurotransmitters and, preferably enzymes involved in the sensation of pain such as, for example, SChE or acetyl cholinesterase, or derivatives of these compounds such as, for example, butyl cholinesterase, or combinations thereof. Compositions may comprise combinations and mixtures of any or all of the foregoing. Preferably, compositions that comprise acetylcholine (ACh) or another pain-associated marker that is useful in the treatment of pain, are administered extradurally or epidurally.

Alternatively, compositions may comprise agents that alter the concentration, absolute amount or activity of a pain-associated marker. For example, such agents include ACh modulators or derivatives. Preferably, such agents specifically and selectively affect that activity of pain-associated marker involved in the perception of pain experienced by a patient and not other activities of the marker. Accordingly, these markers and/or agents are useful, not only to relieve pain, but also to modulate the perception of pain. Preferably, compositions that comprise cholinesterase or another agent that alters the amount or activity of a pain-associated marker and is useful for the treatment of pain, are administered intradurally or subdurally. By administering therapeutically effective amounts of such compositions over a period of time, wherein dosages may remain constant or change in response to perceived physiological conditions, the degree of pain perceived by the patient can be modulated and controlled. In doing so, preferably such compositions do not directly cause or indirectly induce harmful side effects attributable to conventional therapies such as opiate treatment or therapies attributable to the simple administration of neurotransmitters which may themselves increase pain. Also, the modulation of pain can make chronic pain, when not completely eliminated, at least manageable. Preferably such compositions have the advantage that the patient does not become sensitized or desensitized to treatment as markers and agents are natural (i.e. not artificial) components of the patient's system. Thus, therapeutically effective amounts are relatively constant over time for selected patients or groups of patients or at least patients that share a common environmental or genetic characteristic or predisposition.

In a preferred embodiment, the composition comprises the pain-associated marker cholinesterase and, more preferably, SChE which is prepared in an amount and concentration appropriate for administration to a patient. That amount may be determined by the amount of pain perceived by the patient. Alternatively, the composition comprises an agent that specifically alters the activity of ACh. In a more preferred embodiment, the pain-associated marker inhibits pain by inhibiting the pain-associated activities of ACh without inhibiting other activities of ACh.

Markers or agents may be formulated in compositions in an amount and concentration such that the active ingredient therein is therapeutically effective for the treatment of pain. The therapeutically effective amount may be determined by the amount or concentration of a pain-associated marker obtained in a biological sample taken from a patient. Preferably the patient from which the biological sample is obtained, and thus the therapeutically effective amount is determined, is the same patient who is ultimately administered the composition. Compositions may further comprise a pharmaceutically acceptable carrier such as, for example, water, alcohol, oil, saccharide, starch, cellulose, fatty acid, lipid or combinations of any such carriers or other inert ingredients.

Compositions of the invention may be administered as powders, capsules, tablets, sprays, suspensions or liquids, or as a combination thereof. Compositions may also be formulated for slow release or timed release after administration to the patient. Such compositions may be formulated to be administered orally, parentally or topically as necessary and appropriate to provide maximal effect to relieve the perception of pain.

Another embodiment of the invention is directed to a method of treating and thereby relieving pain being perceived by a patient. Methods comprise administering a composition to the patient containing a therapeutically effect amount of a pain-associated marker or, alternatively, agent that affects the perception of pain in the patient. Both the specific marker or agent, and the amount of that marker or agent administered may be determined by the presence and/or activity of a pain-associated marker in a biological sample obtained from the patient. The presence and/or quantity of the marker can be used to determine a therapeutically effective dose of the composition which will be effective for the patient. For example, high levels of the marker in a sample are indicative of high levels of pain in the patient or, in some cases, pain in respective tissue. In such cases, correspondingly high levels of the pain relieving composition will also be required to alleviate the pain. In situations where there is a low level of pain, the type of pain relief administered may be mild. Milder treatments for pain typically have fewer, if any, of the undesirable side effects usually associated with more powerful pain relief. Of course, the same composition may simply be administered at a fairly low dose. Compositions that are administered may be conventional, in other words well-known pain relieving compositions, or compositions of the invention that directly or indirectly block the progression of pain in the patient. Both conventional compositions and novel compositions of the invention may be administered systemically or locally, as needed, to block or at least decrease the sensation of pain. Local administration is most effective when the dose and type of medication is correlated with the perceived pain. In such instances, a sample obtained from the area or tissue of interest is obtained and the presence and/or amount of a pain marker determined. From that data, the most effective composition and most effective amount of that composition can be administered to the affected area. The sample may be selected from the group including, but not limited to, blood, serum, lymph fluid, tears, semen, intracellular fluid, extracellular fluid, interstitial fluid, cerebrospinal fluid, sweat, urine and saliva.

Compositions may be administered to a patient in a variety of forms such as, for example, by ingestion, parenteral administration, topical application or a combination thereof Ingestion may involve capsules, granules, tablets, suspensions, liquids or combinations thereof. Parenteral administration may involve injection of compositions into the blood stream, cerebrospinal fluid or localized areas of the body such as in organ transplantations. Local administration may involve injection or otherwise direct application of the composition to nerves, nerve fibers or nerve roots or to areas with a high concentration of such nerve tissues. Compositions may also be administered to patients by extradural, epidural, intradural or subdural means. Intradural or subdural administration is preferred for compositions containing agents that inhibit the pain-associated activities of a pain-associated marker such as, for example, acetylcholinesterase that inhibits the pain-associated activities of ACh. In contrast, epidural or extradural administration is preferred for compositions containing a pain-associated marker such as, for example, the neurotransmitter ACh.

Topical application may involve administration of a cream or ointment directly to the area of interest. Compositions may also be administered as a single bolus in what would otherwise be considered as an unnaturally excess amount for shock therapy to over-stimulate the nervous system, either locally or systemically, and thereby shut down the generation of the sensation of pain perceived by the patient.

Once administered to the patient, the composition can be released either systemically for general dissemination throughout the body, in a timed-release fashion or targeted for local administration. For example, compositions may be targeted to specific regions of the body for the treatment of acute or chronic pain in or associated with, for example, organs, the skin, the throat, joints, the nose, muscles, neuromuscular junctions, nerves, cholinergic fibers, synovial membranes, genital or anal areas, the uterus, ligaments, the mouth and specific nerves of the jaw and teeth (e.g. which may be targeted during dental surgery), the cornea, the ears or the gastrointestinal tract. The organs treated by the present invention may be internal organs such as, for example, kidneys and the liver, or they may be sense organs, such as the eyes. Mucous membranes may also be targeted for treatment by the present invention. For example, the mucous membranes of the nose can be targeted by use of a nasal spray. Nerves that may be treated with the present invention include, but are not limited to, a cranial nerve, such as the trigeminal nerve, optic nerve, sciatic nerve, ophthalmic nerve, vertebral nerve or a spinal nerve. Any one or more of a plurality of pain types may be treated by the present invention, including, but not limited to, chronic spinal pain, menstrual pain, pain associated with auto-immune disease, muscle cramps and spasms, stomach pain, tooth pain and combinations of these types of pain. The present invention may also be used to treat the pain brought on by afflictions of the nervous system, such as pain caused by diabetic neuropathy, immune disorders and auto-immune disease.

Other embodiments and advantages of the invention are set forth, in part, in the description which follows and, in part, will be obvious from this description and may be learned from practice of the invention.

EXAMPLES

Example 1

Subject Selection.

To determine if there is a statistically significant association of SChE levels with the pain of chronic spinal pain, the SChE levels of chronic spinal pain patients were monitored. Chronic spinal pain is defined as spinal pain and suffering of more than six months' duration. Currently, there is no objective laboratory finding correlating SChE with chronic spinal pain.

Informed consents were obtained from all patients and control volunteers in this study. Ninety-six subjects were studied in four groups: Group one comprised of 55 chronic spinal pain patients, 37 males and 18 females, with ages between 20 years to 81 years with a group average age of 51 years. The patients in this group were undergoing surgery for chronic spinal pain. Group 2 comprised of 11 surgical controls, six females and five males, with ages between 27 years to 70 years with a group average age of 52. The patients in this group were operated for a painless problem (e.g. a face-lift) and there were other cases that had no pain; Group 3 comprised of nine legally disabled chronic spinal pain patients, seven males and two females. Group 3 had an average age of 54 years and a range of 48–58 years, who received compensation or social security payments for over a year, but were otherwise healthy. Group 4 comprised of 21 healthy pain-free controls, 11 males and 10 females with an average age of 45 years and a range of 22–65 years.

Subjects that were uncooperative or pregnant, and patients that showed serious general diseases, other trauma, or abnormal conditions involving muscle or brain were not included in the study.

Example 2

Sample Handling

In most cases, blood was collected directly from the antecubital fossa of a patient. In some cases, blood was collected from an intravenous (IV) line if the patient was in the hospital for another procedure. Five ml of blood was placed in a glass vial, (VACUTUBE™; Bectol-Dickenson, Franklin Lakes, N.J.) and allowed to coagulate for 15 minutes at room temperature. After coagulation, the blood was centrifuged at about 783×g (2500 RPM) for 10 minutes at room temperature. Serum was transferred using a glass pipette into a storage tube and placed into a −20° C. freezer and within one hour. For long term storage, serum was frozen in a −70° C. freezer.

Example 3

Analysis of Serum Cholinesterase

SChE level was determined by a commercial laboratory using the following procedure. Briefly, 20 microliters of serum was mixed with 40 microliters of a 25% (w/v) sucrose solution containing 10 mM Tris-formate at pH 9.0. Three microliters were placed into each well of a vertical polyacrylamide slab. The polyacrylamide gel used was a 6.5 percent T, 5.0 percent C gel. Electrophoresis was performed using a discontinuous sulfate-borate buffer system. Following electrophoresis, the gel was placed in 96 ml of 0.2 M Tris-chloride, pH 6.6, in the presence of FAST Red TR (4-chloro-2-methylaniline, Sigma, St. Louis Mo.) as the diazonium salt for five minutes. Four ml of a 1.0% sodium alpha naphthyl acetate in an acetone solvent was added and the reaction was carried out for ten minutes at room temperature with constant agitation.

The results were analyzed using published procedures (Allen R. C. In: Allen R. C. and Maurer H. R., ed. Polyacrylamide Gel Electrophoresis and Isoelectric Focusing. Berlin: de Gruyter, 287–97 (1974); Allen R. C. and Moore D. J. Anal Biochem., 16:457–62 (1966); Allen R. C. et al., J. Histochem. Cytochem., 13:249–53, 1965). Briefly, the reaction was stopped with 10% acetic acid and the resulting insoluble diazonium complex bands of esterase activity analyzed by quantitative microdensitometry using a CCD device coupled to a Macintosh 8600 computer. Processing and analysis of the digital pattern was performed by computer analysis. Densitometric results are presented as units of activity per 3 $\mu l$ sample directly from the integrated area under the curve of each peak expressed in pixels.

Example 4

Analysis of Results

From the results of Example 3, only the major serum esterase, which is eserine sensitive, was measured. There was no significant difference in the preoperative SChE levels of males and females in either the chronic spinal pain patients (males=1383; females=1252) or in the normal controls (males=904±139.9) (females=978.9±82.8), although male levels were higher in the pain group. This result was contrary to published reports (Allen R. C. and Moore D. J., Endocrinology, 78:655–60, 1966; Los L. E. et al., Drug Metabolism & Disposition, 24(1):28–33, 1996; Tuovinen K. etal., General Pharmacol., 29(3):333–5, 1997). The mean of 21 controls was 941±110. Each patient was run on a single series to eliminate integral variation in esterase activity. However, control values of a single serum sample on 33 separate gels was 901.1±50.5 units expressed as the integrated area under the curve expressed in pixels. Age was not a significant factor in the preoperative SChE levels. Above 60 years, the mean level was 1335; below 60 years, it was 1350.

The mean preoperative SChE level (1341) of the chronic spinal pain patients was significantly higher than: 1) the preoperative mean level of SChE (1180) in the surgical controls (p=0.010); 2) the mean SChE level (941) of the normal controls (p<0.001); and 3) the mean (1184) of the disabled patients (p=0.010). These results are plotted in FIG. 1 which shows the significant differences between the preoperative SChE levels of the chronic spinal pain patients and controls, and between the disabled patients receiving compensation for over one year. The significant difference between the preoperative SChE level of the surgical controls and healthy controls was probably due to the stress incurred by the former while awaiting surgery. This suggested that stress, pain and suffering may have a cholinergic basis. The level of SChE in the disabled patients is equal to that of the surgical controls. As depicted in FIG. 1, there was a significant difference between the mean preoperative SChE level of the surgical controls and normal controls (p=0.0068).

Figure 2:
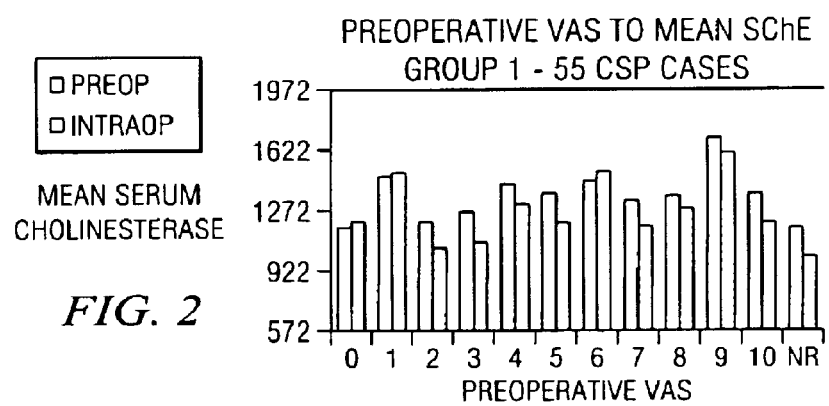
FIG. 2 Preoperative VAS to mean SChE levels in group 1 cases.

The mean preoperative SChE level of the chronic spinal pain patients (1241) with a visual assessment scale (VAS) of less than or equal to 2 was lower, but not significantly lower, than patients with a VAS of more than 2 (1364). A significant intraoperative drop 30 minutes post-anesthetic induction of the preoperative SChE level was noted in patients with a VAS of more than 2 (p<0.001). This drop was not significant in patients with a VAS of less than 2. As shown in FIG. 2, SChE level was significantly (p=0.001) lower than the intraoperative SChE level. In one case, the VAS was not recorded, but did show a drop in SChE level with anesthesia.

Figure 3A:
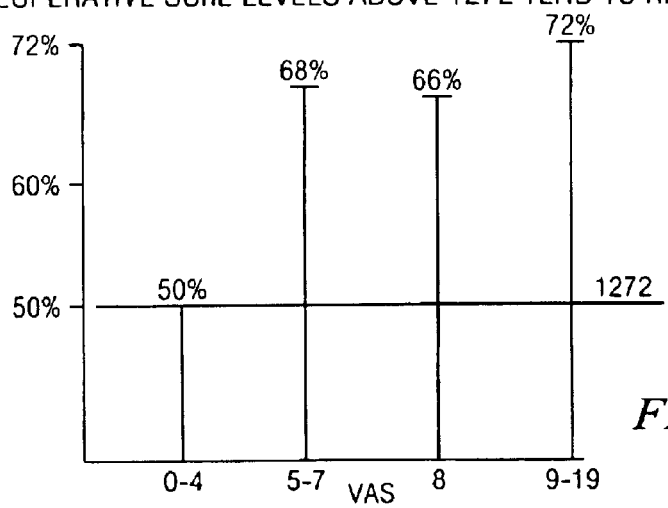
FIG. 3(A) Correlation of VAS with SChE.

If the mean of the preoperative SChE level was less than 1272, the mean of the VAS was lower, but not significantly, than if the preoperative mean was greater than 1272. In patients with a VAS of 0, the mean intraoperative SChE level had only insignificantly changes of less than 30 units. In patients with a preoperative VAS of 10, the mean intraoperative SChE fell significantly 167 units (p=0.004). A 95% compliance level was found for the difference in SChE between the preoperative and intraoperative levels (65–175 units) in chronic spinal pain patients with a preoperative VAS of greater than 2. A trend correlating the VAS and SChE was noted: with VAS scores of 0–4, 50% of the preoperative SChE levels were above 1272; between scores of 5–7, 68% were above 1272; with scores of 8, 66% were above 1272; and between 9–10, 72% were above 1272 (see FIG. 3(A)). One outlying SChE associated with a VAS of 1 was a patient known to use drugs.

With anesthesia, the mean preoperative SChE level of 1341 in the 55 chronic spinal pain patients fell significantly an average of 104 units 30 minutes post-induction (p<0.001) (FIG. 3(B)). This fall was higher for chronic spinal pain males (116 units; p=0.002) than females (78 units; p=0.04), but the difference between the male drop and the female drop was not significant. In contrast, the preoperative SChE level of the 11 surgical controls did not change significantly 30 minutes after anesthetic induction (1180 to 1192; p=0.755). The mean intraoperative level (1306) in 13 chronic spinal pain patients fell significantly 147 units to a mean of 1175 on the first PO day (p=0.007). This represented a marked decrease (237) from the preoperative SChE level of 1412 (p<0.001). In these same 13 patients, two significant drops are shown, the first between the preoperative SChE level and the 30 minute intraoperative level; and the second between the intraoperative level and the level on the first postoperative day. The low level of the latter was probably due to the injectable drugs used to control postoperative pain (FIG. 3(C)).

Figure 3D:
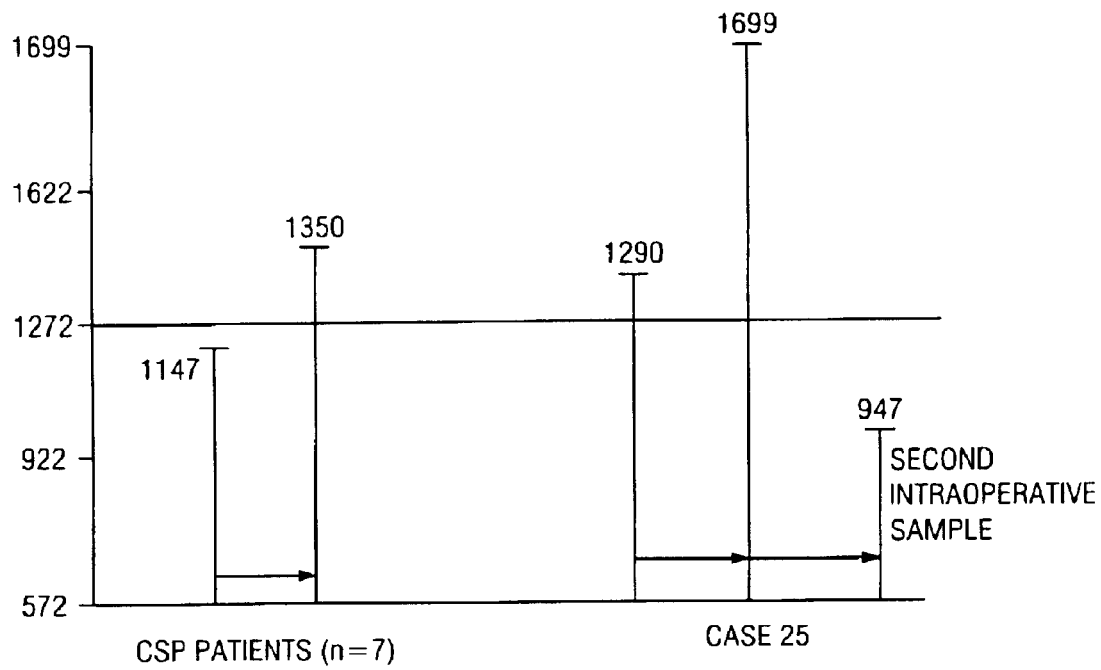
FIG. 3(D) Means of the preoperative and post-induction SChE levels in CSP patients.

The preoperative SChE level of seven chronic pain patients rose a mean of 204 units, (more than two SD above normal controls) 30 minutes after induction. Five were associated with spinal instrumentation and bad an unstable facetectomy. Elevation was probably due to the necessary preoperative positioning of a chronic spinal pain patient with a painful lesion susceptible to this manipulation (see FIG. 3(D)). Five of these cases (Cases 2, 4, 25, 33 and 39) included the utilization of HW, one (Case 35) had an unstabilized facetectomy and one (Case 17) had a discectomy and foramenotomy. The largest rise (409) was in Case 25, a HW removal (FIG. 3(C)). The volatility of case 25 is also shown which illustrates the extreme changes in the levels of SChE that occurred under anesthesia, probably due, in part, when the "painful HW" was aggravated and subsequently removed. After the metal was retrieved, the SChE level fell precipitously 706 units.

Figure 4:
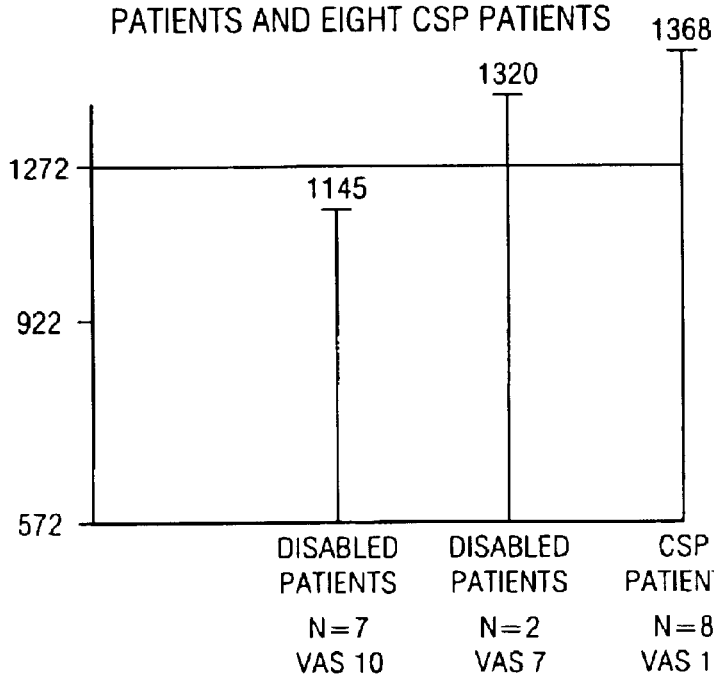
FIG. 4 Mean SChE levels of disabled patients and CSP patients.

Seven of nine disabled patients receiving social security benefits reported a VAS of 10 with mean SChE levels of 1145, which was 200+ units below the mean of the chronic spinal pain patients who also had a VAS of 10 (FIG. 4). These seven cases did not correlate. The remaining two reported a VAS of 7 and their SChE levels were 1350 and 1291, respectively, which correlated. The mean SChE level, 1148, was more than two SD (210 units) below the mean SChE level found in chronic spinal pain patients with a VAS of ten.

These data indicate that, as most patients with pain have SChE levels greater than 1272 (three SD above the mean level of normal controls), this measurement may provide an objective tool to augment the measurement of pain and its physiological effects.

One of the neurochemical pathways from brain to serum for SChE may be through the cerebral spinal fluid, which communicated with the sagittal venous sinus. Cholinergic systems were found to play a possible role in chronic spinal pain (Hudson D. M. et al., Brain Res., 338(2):267–72, 1985; Leeuin R. S. and Zeegers A., Euro. J. Pharm., 101:285–8, 1984; Scali C. et al., Euro. J. Pharm., 325(2–3):173–80, 1997; Vogt M. et al., Neuroscience, 12:979–995, 1984). It is also known that the neuromuscular junctions of the peripheral nervous systems (PNS) have billions of cholinergic synapses. Because there is no significant change from the preoperative to the intraoperative levels of SChE in the surgical controls, it was reasoned that the preoperative to intraoperative change of SChE levels in patients with chronic spinal pain were not associated with the quieting of the neuromuscular junctions with anesthesia and muscle relaxants, as these drugs were administered both to the surgical controls and to the patients being operated for chronic spinal pain. Additionally, it was observed that the preoperative SChE levels in the chronic spinal pain patients were unchanged intraoperatively in 22 cases and elevated in six, which ruled out lowering of the SChE with anesthetic muscle relaxation. Further, the muscle relaxants used, NOCURON™, ROCURONIUM™ and NIMBEX™, are non-depolarizing drugs that acted on the post-synaptic neuromuscular membrane by competing with and blocking the transmission of ACh, and have no effect on cholinesterase (ChE). Rarely used was Succinylcholine that combined with the cholinergic receptors of the motor end plate to produce depolarization, with no effect on cholinesterase.

These data obtained to date indicates that the autonomic nervous system (ANS) did not contribute to the changes of the SChE levels in patients with chronic spinal pain. However, the preoperative mean level of SChE in the surgical controls was significantly higher than the preoperative mean of the normal controls (1180). This elevation may be due to stress induced from the fright or concern of patients going from a painless to a painful environment. It has been reported that stress was related to the autonomic nervous system (Cepeda M. S., Curr. Opin. in Anaes., 8:450–4, 1995; Hata T. et al., Japanese J. Pharm., 41(4): 475–85, 1986). The preoperative levels of these surgical controls did not change with anesthesia. It is possible that anesthesia did not affect the autonomic nervous system or the SChE levels related to stress. Thus, the finding of a SChE level minimally above normal, but below 1272, may be helpful in the evaluation of patients with stress.

A correlation between the VAS and the level of SChE demonstrated the subjectivity of the VAS and the objectivity of the SChE. At the extremes of the curve were patients with a VAS of 0 and a mean preoperative SChE of 1164, contrasted with the patients with a VAS of 10 and a preoperative SChE of 1359. Deviations from the curve may indicate that patients had varying tolerances for pain, or were unable to accurately assess their pain with a number. A patient known to have used drugs, had a preoperative VAS below 6. The results indicate that the VAS is inaccurately subjective whereas the SChE is accurately objective.

There was no significant difference in the SChE levels associated with age or sex although the SChE was slightly higher in males. The intraoperative drop of SChE in 55 chronic spinal pain patients with a mean preoperative level of 1350 was significant in both males and females (FIG. 3(B)) (p=0.002 for both sexes), but not significantly different from each other. This did not agree with published reports (Sharma G. and Sharma S. P. Exper. Aging Res., 7(2) :107–15, 1981).

Figure 5:
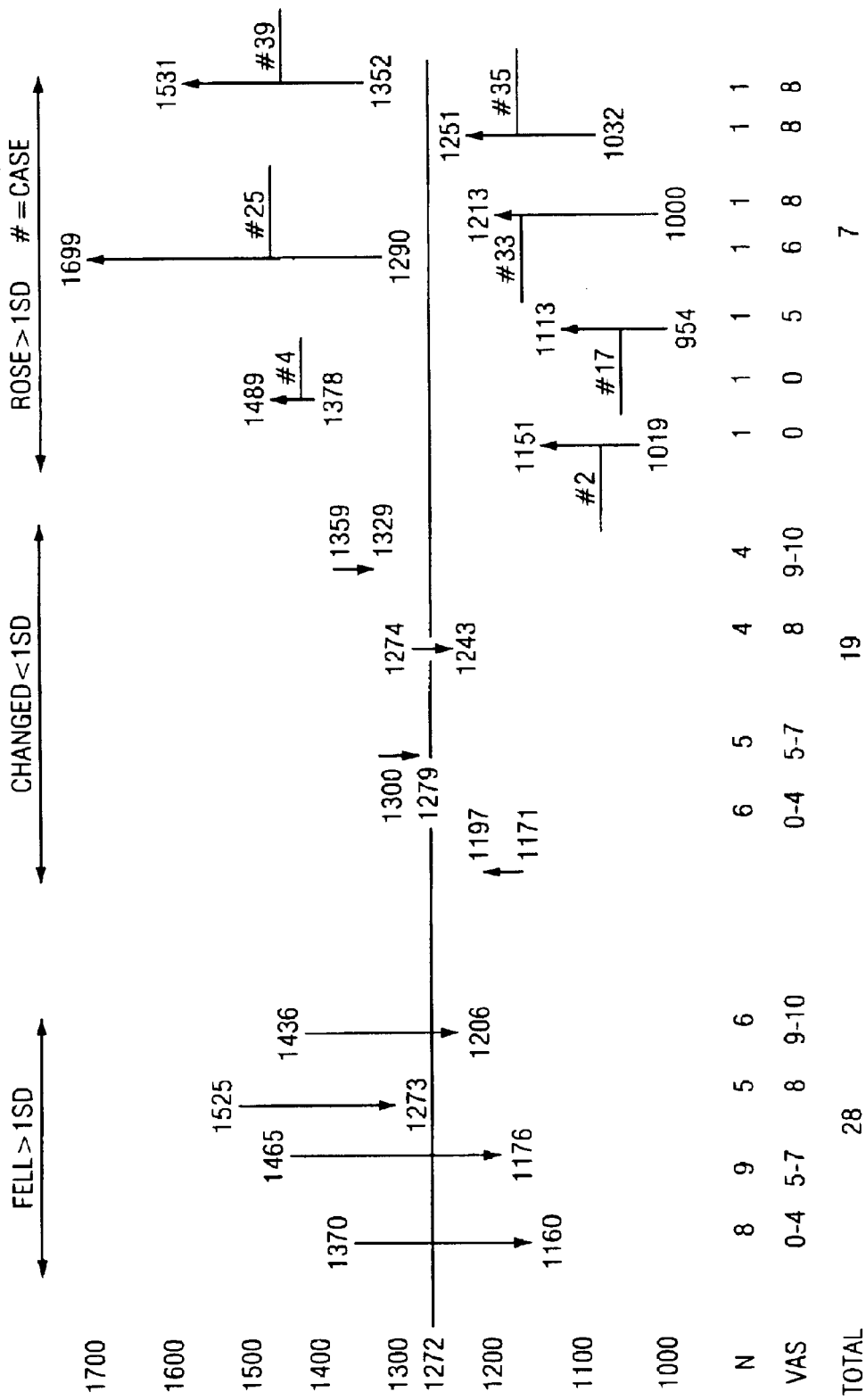
FIG. 5 Preoperative to post-induction SChE levels in CSP patients.

In this study, the preoperative SChE was either above or below 1272, and 30 minutes after anesthetic induction, it either fell more than 1 SD (=100 units), rose more than 1 SD or did not change more than 1 SD (FIG. 5). Intraoperative levels were not fixed and rose, probably in response to noxious stimulation as noted in the Vogt study, or fell with the removal of such stimulation.

Figure 6:
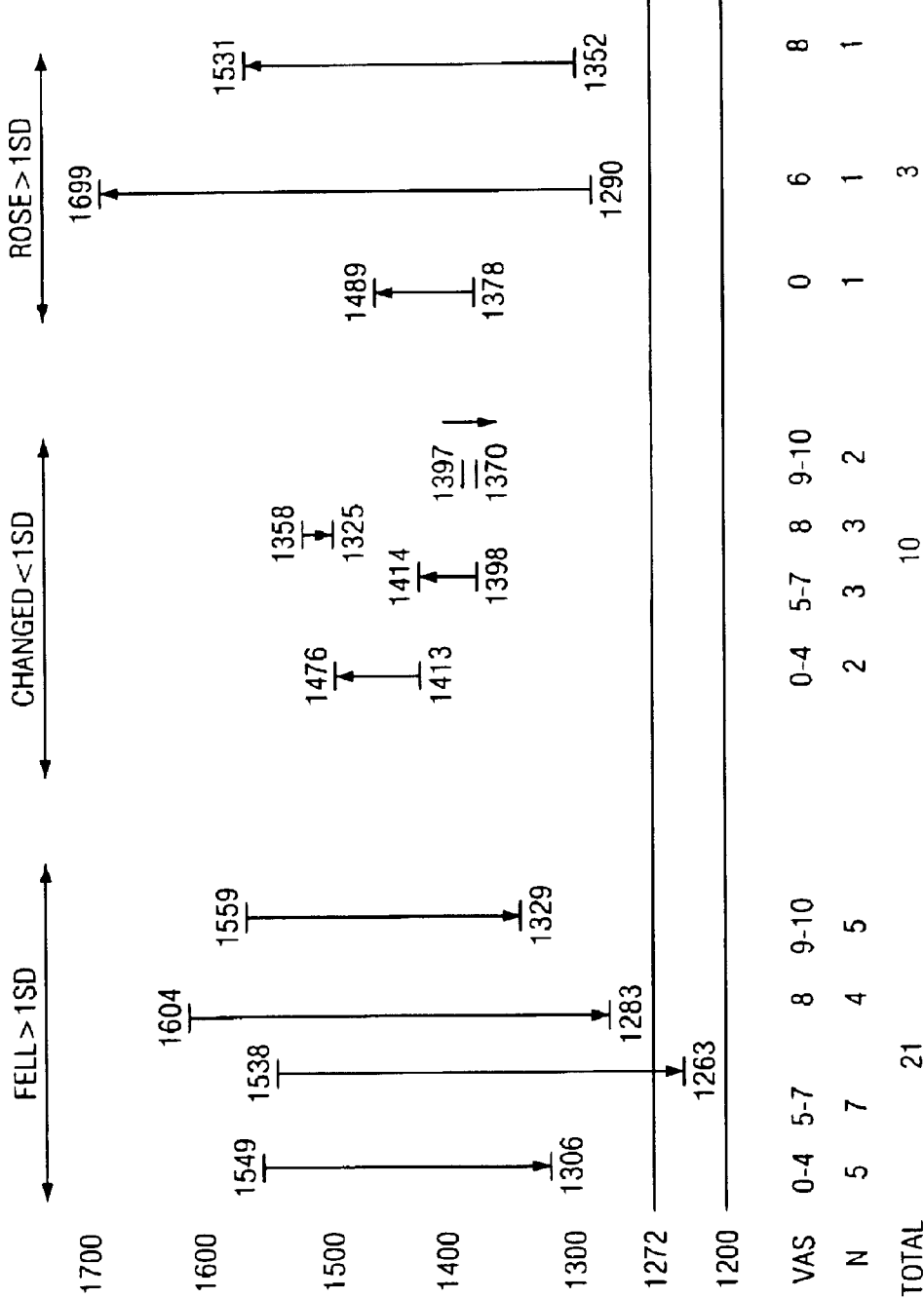
FIG. 6 Preoperative to post-induction SChE levels in CSP patients with preoperative levels greater than 1272.

The preoperative SChE was above 1272 in 34 of 55 cases (i.e. 63%) of chronic spinal pain cases (FIG. 6). The VAS was between 0–4 in eight cases; 5–7 in 11 cases; 8 in eight cases, and 9–10 in seven cases. Of this group of 34, the SChE level fell more than one SD 30 minutes post-anesthetic induction in 21 cases (62%), rose more than one SD in three (9%), did not change more than 1 SD in ten (29%). The 21 cases with falling levels of SChE probably had a reduction of the cholinergic neuronal activity associated with chronic spinal pain. All of the cases with rising intraoperative SChE levels were associated with instrumentation (Case 4, VAS of 0, SChE 1375; Case 25, VAS of 6, SChE 1290; and Case 39, VAS of 8, SChE 1352). The preoperative VAS and SChE values correlated in Cases 25 and 39, but not in Case 4 as this patient had taken analgesic drugs shortly before the initial venipuncture.

The SChE levels in the above ten cases that changed less than 1 SD intraoperatively correlated with the VAS, as two scored 1 (Case 5, SChE 1348 and Case 6, SChE 1578); three scored 5–7 (Case 24, SChE 1283; Case 26, SChE 1442, and Case 31, SChE 1471); three scored 8 (Case 38, SChE 1316; Case 40, SChE 1367, Case 41, SChE 1392) and two scored 9–10 (Case 46, SChE 1743 and Case 51, SChE 1337). The mean of the preoperative SChE levels of these 10 cases was elevated 2 SD above 1272 (1428). This may have indicated the presence of sensitive pain-producing lesions that prevented an intraoperative drop of SChE. The lesions may have been stimulated by the vigorous, preoperative manipulation necessary to position lumbar and thoracic surgical patients, or by the preoperative application of tongs and traction for cervical spine cases.

Five of these 10 cases were associated with instrumentation (Cases 24, 31, 40, 41 and 51). One had a herniated disc in a multiply-operated lumbar spine with adhesions (Case 38); one had multiple discectomies (Case 46); one, the oldest patient (78 yrs.) (Case 5), and Case 26 had laminectomies (LAM), and one had a LAM and fusion but expired with a post-operative pulmonary embolism (Case 6).

In 20 of the 55 chronic spinal pain patients (36%), the preoperative SChE was below 1272 (FIG. 7). In eight the VAS was 0–4; in five it was 5–7; in four it was 8; and in three it was 9–10. Of this group, the 30 minute post-anesthetic intraoperative SChE level did not change more than 1 SD in nine cases (45%), fell more than 1 SD in seven (35%), and rose more than 1 SD in four (20%). Of the four with rising SChE intraoperative levels, two were associated with instrumentation (Case 2, VAS of 0, SChE 1019; and Case 33, VAS of 8, SChE 1000), and one had a discectomy (Case 17, VAS 5, SChE 954), and one had a lumbar LAM with a facetectomy (Case 35, VAS of 8, SChE 1032). The VAS and SChE in Cases 33 and 35 did not correlate, whereas Case 2 did.

The mean of the preoperative SChE of the above nine patients that had less than one SD intraoperative change of SChE was 1076, more than two SD below 1272. This may have indicated that the pathological lesion was minimally sensitive, did not stimulate the cholinergic nervous system and was not stimulated by preoperative, positional manipulation. Three of these nine had a simple LAM and disc excision (Cases 1, 11 and 14 with a preoperative VAS of 0–4 and mean SChE of 1109) and one (Case 49, VAS of 10, SChE 1208) had a lumbar discectomy and facetectomy. Two had anterior cervical fusions (Case 10, VAS of 3, SChE 876 and Case 19, VAS of 5, SChE 1233). One had a decompression of a lumbar stenosis (Case 48, VAS of 10 and SChE level of 1148), and two were associated with lumbar instrumentation (Case 28, VAS of 7, SChE 969 and Case 34, VAS of 8, SChE 1026). Minimal correlation between VAS and SChE was noted in the Cases with a VAS of 0–4 and in Cases 19, 48 and 49. No correlation was noted in Cases 10, 28 and 34.

In seven cases of the 20 that had a falling intraoperative SChE of more than one SD, one had a lumbar decompression (Case 3, VAS of 0), and four each had a LAM and discectomy (Cases 7 and 8, VAS of 2, Case 18 VAS of 3, and Case 29, VAS of 7). Two were associated with instrumentation (Case 36, VAS 8 and Case 47, VAS 10). The preoperative mean level of the preoperative SChE of these seven cases was 1126, slightly 1' SD below 1272. This suggested that 1272, which is three SD above normal and was proposed as the level of SChE above which pain was noted in most chronic spinal pain patients, may be very conservative. These seven cases demonstrated a reduction of the cholinergic neuronal activity associated with chronic spinal pain as was noted in 21 of the 35 cases in which the preoperative SChE was above 1272.

Instrumentation was employed in 15 cases. However, only the sequential intraoperative changes that were studied progressively in 11 cases during the surgery are noted here. These intraoperative changes of SChE were volatile during the course of the surgery (FIG. 8): more than one SD in Cases 41 and 55; more than two SD in Cases 31 and 33; more than three SD in Cases 39 and 51; more than four SD in Cases 4 and 40; more than five SD in Case 44; more than eight SD in Case 42; and more than 10 SD in Cases 25 and 47. The SChE rose with insertion of HW in three patients (Cases 33,42 and 47), fell with the removal in six (Cases 25, 31, 39, 40, 41 and 55); fell with insertion of HW in two (Cases 44 and 51); and rose with a difficult removal of the HW in one (Case 4).

It was concluded that the use of HW probably caused a stimulation of the cholinergic nervous system that produced marked perturbations in the intraoperative SChE concentrations. The rise of intraoperative SChE was not incisional, as the surgical controls and some of the chronic spinal pain patients showed no such elevation of the intraoperative SChE.

The significant fall of SChE ($p<0.001$) on the first postoperative day in 13 patients was probably due to the use of injectable analgesic drugs. These were weaned on the second postoperative day in preparation for hospital dismissal and the SChE level subsequently rose (FIG. 3(C)).

It is reasonable to conclude from the data, which showed no correlation between the SChE levels and the VAS scores in seven of the nine patients receiving monetary benefits for chronic spinal pain, that SChE levels and VAS scores may be of value in screening patients who may be suffering from functional complaints from those who have non-functional chronic spinal pain (FIG. 4).

Research supports the concept of involvement of the cholinergic system of the brain in the appreciation, VAS, and pain and suffering (including the pain of chronic spinal pain) in the conscious patient. The concentrations of SChE in the extracellular spaces and cerebral spinal fluid in brains of mammals have been proven to increase with noxious stimulation, and to diminish with cessation of the stimulus. It is, therefore, reasonable to hypothesize that chronic spinal pain of six months duration or longer could stimulate the cholinergic system of the brain of a human and produce the same changes in the concentrations of cholinesterase in the cerebral spinal fluid and extracellular spaces. Anatomical pathways were hypothesized that may facilitate the movement of cholinesterase from the brain to the serum. Thus, the variations in the levels of SChE and the VAS scores of the patients with chronic spinal pain may have reflected the variations in the concentrations of SChE in the cerebral spinal fluid and extracellular spaces of the brain associated with the stimuli producing the pain of chronic spinal pain.

Thus, these data indicate that SChE levels, which are objectively determined, may be used to quantitate measurements of chronic spinal pain, and may also be helpful in managing patients with chronic spinal pain.

Example 5

Individual Case Reports of Patients

Group 1: VAS=0; n=4; SChE mean=1164

Case 1 (1564): This case had a VAS of 0 and a low preoperative SChE. The intraoperative level was unchanged, suggesting a placebo effect. One month later he returned to work.

Case 2 (1536): This case had hardware usage and a rising intraoperative SChE. Three months later the SChE was higher than the initial preoperative level and the visual assessment scale was 3 with pain. This indicated a guarded outcome. This patient complained of pain four months postoperative.

Case 3 (1537): This case had a 195 unit drop with anesthesia. On the second postoperative day, the SChE rose above the preoperative SChE level. This was not unusual as patients are removed from intravenous and intramuscular injections for pain in preparation for hospital dismissal. The patient returned to work 4 months postoperative. This demonstrated an excellent biochemical indication (BCI) for a biochemical correction.

Case 4 (1558): This case had an elevated preoperative SChE indicating marked pain, which she controlled with drugs. The Intraoperative level increased, suggesting preoperative drug use and/or the vigorous surgery associated with difficult hardware removal. She was treated for postoperative infection, and for three months had persistent pain.

Cases 2 and 4 demonstrate the elevation of SChE frequently seen with patients treated with hardware. Both had pain postoperative at 3 month and 4 months respectively.

Case 3 has a high preoperative SChE that fell with anesthesia. The SChE was elevated the 2nd postoperative day when injectable drugs were stopped, and returned to work 4 months postoperative. Suggests that 1272 may be a conservative figure.

Group 2: VAS=1; n=2; mean=1463

Both cases demonstrated a high tolerance for pain.

Case 5 (1578): This case showed a high preoperative SChE, which increased the SChE level with anesthesia. The first postoperative level was higher than the preoperative SChE level. Two months postoperative the patient continued with chronic spinal pain, and the outcome was guarded.

Case 6 (1575): This case had a high preoperative SChE indicating a high pain tolerance. There were 25 Intraoperative unit drops, but day 1 postoperation the SChE level was low. No follow-up as the patient expired with a massive pulmonary embolus.

Group 3: VAS=2; n=3; mean=1195

Case 7 (1525): The low VAS and a SChE that changed less than 1 SD with anesthesia. One month postoperative she reported a reduction in sciatica, and did not return for further visits. The chance for a biochemical cure was not robust.

Case 8 (1514): The low preoperative SChE did not offer a chance for a surgical cure. The SChE level fell with anesthesia, but one month postoperative it rose above the preoperative level, and two months postoperative she complained of pain. The result was guarded.

Case 9 (1541): An elevated preoperative SChE level that fell with surgery. After the two month old recurrent disc fragment was removed, the SChE fell another 154 units, possibly signaling the removal of a pain-producing mechanism. On the first postoperative day there was an equivocal rise from the intraoperative level to a level well below the initial one. This case demonstrated an excellent BCI surgery. Six weeks later he returned to work.

Group 4: VAS=3; n=4; mean=1249

Case 10 (1547): A low preoperative SChE level and low VAS signaled a minimally pain-producing lesion. The SChE fell less than 1 SD with anesthesia, and five months later she had no pain. Perhaps this was a placebo effect. Six months postoperative she was in a MVA and had a reoccurrence of pain.

Case 11 (1566): The initial level, less than 1 SD below 1272, changed less than 1 SD with anesthesia which suggested that 1272 may be a conservative number for pain. One month later he returned to work.

Case 12 (1553): This case was an ideal case with a high preoperative SChE that fell over 200 units with anesthesia. Two weeks later the level was below the initial level, and six weeks postoperative she was pain-free.

Case 13 (1557): This case had an elevated preoperative level that fell almost 500 units with anesthesia. However, the patient developed acute anxiety and three months postoperative had insomnia and sought psychiatric therapy. The level of SChE, 1234, could be associated with stress.

Group 5: VAS=4; n=3; mean=1409

Case 14 (1522): This case demonstrated a probable low tolerance for pain and a poor BCI. There was a minimal SChE drop with anesthesia. The two-months postoperative SChE level was higher than the preoperative SChE level. In addition, the patient had pain.

Case 15 (1560): This case had a high preoperative SChE that dropped 199 units with anesthesia. At six months he returned to work with no pain. This was a successful case with a high BCI for surgery.

Case 16 (1577): This case had an excellent BCI for surgery. The high preoperative SChE level fell 201 units with anesthesia. On the first day postoperative, the SChE level was lower than the initial one (VAS 7), but rose with postoperative pain on the second day (VAS 4) when the injectable drugs were discontinued in preparation for hospital dismissal. Two months later there was no neck or arm pain.

Group 6: VAS=5; n=7; mean=1359

Case 17 (1538): A workman's compensation (WC) case with a low preoperative, sub-threshold (threshold is referred to as 1272) SChE level that rose with anesthesia. This did not offer a strong opportunity for a biochemical cure. Five months later the patient had not returned to work after a simple discectomy.

Case 18 (1573): A preoperative level that fell 2+SD with anesthesia. During surgery he developed a dural leak that was repaired with a second procedure. Five months postoperative had chronic spinal pain and a VAS of 5–6.

Case 19 (1543): This case was an epileptic on medication who showed a minimally subthreshold preoperative SChE that was unchanged with anesthesia, indicating a lesion that may have been irritated with manipulation. The first day postoperative, the SChE level was 163 units below the Intraoperative level, which was favorable. Three months later he reported no pain.

Case 20 (1567): A one-time previously operated spine with a preoperative SChE level slightly above threshold that fell 1+SD intraoperatively. Six months later he had a VAS of 1 to 2 and returned to work.

Case 21 (1552): This case had a high preoperative SChE level that fell 272 units with anesthesia. One week later the SChE level was only 11 units below the preoperative level; two months postoperative he reported a VAS of 6 and that the pain was the same as his preoperative pain. Five months postoperative his VAS was 7. This suggested a complication of surgery.

Case 22 (1569): A high preoperative SChE level that dropped almost 200 units with anesthesia signaled an excellent chance for a biochemical cure. Six months later he had chronic spinal pain with a VAS of 3–4. This suggests severe pain-producing pathology that could not be completely corrected.

Case 23 (1563): An extremely high preoperative SChE level that fell almost 600 units with anesthesia, suggested an opportunity for a biochemical cure in a multiply operated spine. Extensive surgery was performed and one month later he was improved, but took pain medication. This suggested that SChE levels in the multiply operated spine may be less useful than in virgin spine.

Group 7: VAS=6; n=4; mean=1275

Case 24 (1551): The initial SChE, slightly above threshold, rose with anesthesia in an operation utilizing hardware. Two months later the SChE level was above the preoperative level and the patient was using codeine. Six months postoperative the VAS was 6 to 10, and he attended a pain clinic. There may be an adverse effect of hardware on the SChE.

Case 25 (1561): A multiply operated back with a high preoperative SChE level in an elderly female that rose 4 SD while removing hardware. After the removal of the hardware, the intraoperative SChE fell 6 SD. She was rated with a 60% PPD in follow up with a VAS of 0.

Case 26 (1554): This case had a high preoperative SChE level unchanged with anesthesia. He returned to work 16 months later. This may have indicated a painful lesion aggravated with postural manipulation.

Case 27 (1535): This case had a high preoperative SChE that fell 241 units 30 minutes post-induction, and another 123 units after the removal of a massive disc. This signaled an excellent BCI for surgery. Six weeks later there was some discomfort in the opposite leg.

Group 8: VAS=7; n=5; mean=1427

Case 28 (1523): This case was a multiply operated back with a low preoperative SChE level that rose minimally with hardware removal. Two months later she returned to work with no pain. The preoperative SChE may have indicated that initially, the hardware was minimally painful.

Case 29 (1540): A minimally sub-threshold SChE level that fell 109 units with anesthesia. On the first postoperative day the SChE level was below the intraoperative SChE level (VAS 1). Within two weeks she was pain free and placed on a PRN return basis. This may indicate that 1272 is a conservative threshold level for SChE.

Case 30 (1517): This case had a minimally elevated preoperative level above threshold that fell 281 units with anesthesia. Two months postoperative, the SChE level was below the preoperative level, and the patient had no leg pain.

Case 31 (1530): This case was a multiply operated back admitted for painful hardware removal. The preoperative SChE level was unchanged 30 minutes after induction, but after the hardware (HW) was removed, it fell 138 units. One month postoperative, he complained of pain (VAS 7), and three months postoperative stated that his VAS was 10; but at this time, the SChE was 1183, which made him suspect. He had not returned to work 10 months postoperative. This demonstrated SChE monitoring.

Case 32 (1556): An elderly female with a high preoperative SChE level that showed a BCI for biochemical cure with surgery. The level dropped 231 units with anesthesia, but three weeks postoperative she had pain and used a cane. This demonstrated that SChE may indicate the presence of pain, but cannot prognosticate surgical outcome which depends in great part on the surgeon and his techniques Group 9: VAS=8; n=12; mean=1381

Case 33 (33): A low preoperative SChE which rose 2 SD after anesthetic induction, probably due to the tongs and traction for cervical positioning. Hardware was used with no change in the intraoperative SChE, and 3 months later the patient had chronic spinal pain.

Case 34 (1510): A low preoperative SChE level and high VAS indicate a low tolerance for pain and a poor BCI for surgery. Hardware was used with extensive stabilization, and the patient had pain three months postoperative. This case was not monitored intraoperatively.

Case 35 (1550): This case was under medication for von Willibrand's disease. The initial SChE level rose with induction, and two months later she complained of mechanical pain. This case was not a proper one for the use of SChE levels to determine pain.

Case 36 (1539): A moderately elevated preoperative SChE level that fell 173 units post-induction. An extensive eight-hour procedure with hardware was performed, No repeated intraoperative monitoring was carried out. Four months later it was reported that her pain was resolved. This indicated the work of a highly skilled surgeon in a virgin back.

Case 37 (1528): The high preoperative SChE level showed that the BCI for surgery was excellent, and the 376 fall with anesthesia confirmed this. Six months postoperative the VAS was 5. This demonstrated that the preoperative SChE level can predict the degree of pain and seriousness of the lesion, but cannot predict the outcome. The outcome was dependent on additional variables such as the surgeon's skill and techniques.

Case 38 (1592): This case had an excellent BCI for surgery. The high preoperative SChE fell 1 SD and the first postoperative SChE was lower than the preoperative SChE. However, scarring from previous surgery probably caused the pain and RAD and a VAS of 4 two months postoperative, with no returned to work.

Case 39 (1559): This case showed a rise of the preoperative SChE level with anesthesia that was frequently associated with the preoperative postural manipulation patients with painful hardware. The intraoperative SChE level fell 1 SD after the hardware was removed, and two months later the patient had chronic spinal pain.

Case 40 (1601): The high preoperative SChE was unchanged with 30 minutes after anesthesia in a patient operated for removal of painful hardware from the lumbar spine. However, when the hardware was removed, the intraoperative SChE fell 4 SD On the first postoperative day, the SChE was below the initial preoperative level, but the VAS was 7. The patient had CSP two months later.

Case 41 (1596): The high preoperative SChE in this multiply operated back with adhesions rose intraoperatively with anesthesia. Both the SChE level and VAS fell on the first postoperative day but rose on the 2nd postoperative day. Six months later, pain and RAD persisted. This suggested that adhesions elevate SChE levels.

Case 42 (1607): This case had an excellent BCI for surgery with a high preoperative SChE that fell 559 units with anesthesia. When hardware was inserted, the SChE rose 2 SD. Six weeks later, he was using pain medication.

Case 43 (1532): Illustrated an unsuccessful outcome in a case operated for two HNP. The BCI was present, and the intraoperative SChE was 1 SD below the preoperative level, but above 1272. Two months stated that his pain was the same as the preoperative pain (VAS 8).

Case 44 (1576): This case had an extremely high preoperative SChE that fell with anesthesia and subsequently during the prolonged surgery utilizing hardware. All intraoperative levels were above 1272. Five months postoperative the patient had pain and a VAS of 7–8.

Group 10: VAS=9; n=2; mean=1381

Case 45 (1571): This case had an excellent BCI for surgery with a high preoperative SChE level that fell 250 units with anesthesia and on the first postoperative day, the VAS was 0 and the SChE level 305 units below the preoperative SChE. One month later he was painless and dismissed on a PRN basis. This was excellent SChE and clinical picture correlation.

Case 46 (1548): This case had a high preoperative SChE that rose with anesthesia. This was an excision of two HNP's in a patient who returned to work, but 13 months later had minimal pain.

Group 11: VAS=10; n=8; mean=1432

Case 47 (1519): A poor BCI for surgery with a preoperative SChE below threshold. The SChE level dropped 30 minute after induction, but rose almost 800 units during surgery with the use of hardware. Eight months postoperative he was attending a pain clinic. This showed the marked reaction to hardware, and that the SChE may be a helpful indicator for surgery.

Case 48 (1598): An elderly patient with a minimally subthreshold preoperative SChE that was unchanged 1 SD 30 minutes after induction, but fell 1 SD on the first postoperative day. One month later he had pain that was less than the preoperative pain, and reported a VAS of 3. This suggests that a threshold of 1272 is conservative.

Case 49 (1545): This case had fair BCI for surgery in a female with a preoperative SChE that was unchanged more than 1 SD after induction, but rose to the preoperative SChE level after removal of the disc and facet. Five months later her SChE level was above the preoperative SChE level, the VAS was 1, and she was taking therapy. The two postoperative SChE elevations may have been associated with an unstabilized facetectomy.

Case 50 (1542): A previously operated spine with arachnoiditis with a preoperative SChE signaling pain The SChE level fell with anesthesia, but two months later the patient had pain. The preoperative SChE probably signaled the presence of legitimate pain and a good BCI that did not and could not predict the surgical outcome.

Case 51 (1546): This case had excellent BCI with a preoperative SChE that fell 1 SD 30 minutes after induction and further with the prolonged surgery necessary for the insertion of hardware. Six months later the patient had back pain with RAD.

Case 52 (1513): An excellent BCI for a biochemical cure that fell 396 units with surgery, and 13 months postoperative had no pain.

Case 53 (1501): This case had an excellent BCI with a high preoperative SChE that fell 237 units 30 minutes post-anesthetic induction in a rheumatoid patient. Two weeks postoperative the VAS of 0 and the SChE level were below the anesthetic level. Two months postoperative he reported a reoccurrence of pain and the VAS was 8, the SChE low. Six months postoperative the VAS was 5 and the SChE rose to the anesthetic level. Eighteen months postoperative the VAS was 0 and the SChE below the anesthetic level. Some of his pain was probably rheumatoid in origin. This demonstrated the monitoring capabilities of SChE.

Case 54 (1603): This case was elderly male with a preoperative SChE that indicated an excellent BCI that fell almost 2 SD units with anesthesia. One month later he was improved with minimal pain and slight loss of strength.

Case 55: A young male with painful hardware. The preoperative VAS was not recorded. The preoperative SChE, which was below 1272, fell 1 SD with anesthesia, rose and fell slightly intraoperatively with the removal of the hardware. Six months later, he complained of a VAS of 8 with a SChE of 1118, which made him suspect. This demonstrated the monitoring qualities of SChE.

1202, 1203, 1204, 1206, 1207, 1211, and 1212 were disabled patients whose VAS and SChE levels did not correlate.

Other embodiments and uses of the invention will be apparent to those skilled in the art from consideration of the specification and practice of the invention disclosed herein. All references cited herein, including all U.S. and foreign patents and patent applications, are specifically incorporated by reference, including U.S. provisional patent application serial No. 60/109,504, filed Nov. 23, 1998 and U.S. provisional patent application serial No. 60/141,255, filed Jun. 25, 1999. The specification and examples should be considered exemplary only with the true scope and spirit of the invention indicated by the following claims.

We claim:

1. A method for identifying a marker that correlates with the intensity of a pain perceived by a patient comprising the steps of:
   collecting a serum sample from the patient;
   separating the components within said serum sample by electrophoresis in a gel;
   reacting the gel with a diazonium salt and a substrate for a period of time to form a detectable band comprising an insoluble diazonium complex; and
   identifying the size and location of the detectable band to identify said marker.

2. The method of claim 1 wherein the gel has a gradient polymer density.

3. The method of claim 1 wherein the diazonium salt is 4-chloro-2-methylaniline.

4. The method of claim 1 wherein reacting is terminated by adding a reagent to the gel wherein said reagent is selected from the group consisting of acetic acid, formic acid and citric acid and mixtures thereof.

5. The method of claim 1 further comprising performing densitometry analysis on said gel.

6. A method of diagnosing the extent of activation of the pain sensing neurological pathway in a patient comprising:
   i) determining the amount of a cholinesterase pain marker in a biological sample obtained from said patient;
   ii) comparing the amount of the cholinesterase pain marker in said sample to a threshold amount of cholinesterase pain marker; and
   iii) assigning a pain status to the patient based upon the comparison, wherein the threshold amount of cholinesterase pain marker is determined by measuring the amount of cholinesterase in samples from patients in whom the pain sensing neurological pathway is not activated and setting the threshold so that the threshold amount of cholinesterase pain marker is at least three standard deviations above the mean cholinesterase amount in samples from normal individuals.

7. The method of claim 6, wherein additional amounts of cholinesterase pain marker are identified as indicative of increasing levels of pain sensing neurological pathway activation by comparing the mean amount of cholinesterase pain marker in individuals with higher levels of pain sensing neurological pathway activation with mean of cholinesterase pain marker in individuals with lower levels of pain sensing neurological pathway activation and selecting an amount between the two means.

8. The method of claim 6, wherein the pain sensing neurological pathway is activated by chronic spinal pain.

9. The method of claim 8, wherein the sample is blood or serum and the cholinesterase is serum cholinesterase.

10. The method of claim 9, wherein threshold amount of cholinesterase pain marker is 1272 and patients from whom the sample contains less than this amount of serum cholinesterase are deemed to have normal activation levels of the pain sensing neurological pathway while patients from whom the sample contains greater than this amount of serum cholinesterase are deemed to have high or activated activation levels of the pain sensing neurological pathway.

11. The method of claim 6 further including the step of separating components within the biological sample.

12. The method of claim 11 wherein separating comprises an electrophoretic separation.

13. The method of claim 6, wherein the cholinesterase in the biological sample is reacted with a substrate to produce a detectable product.

14. The method of claim 6, wherein the threshold amount of cholinesterase pain marker is based upon a normal individual sample obtained from the same patient prior to activation of the pain sensing neurological pathway.

15. The method of claim 6, wherein the activation of the pain sensing neurological pathway is caused by the presence of a lesion.

16. The method of claim 6, whereby cholinesterase is distinguished and measured by escrine sensitivity.

17. A diagnostic kit for determining the level of activation of the pain sensing neurological pathway in a patient comprising at least one antibody that binds to cholinesterase in a biological sample obtained from the patient wherein the amount of cholinesterase in the sample is then compared with an amount of cholinesterase known to be indicative of activation of the pain sensing neurological pathway.

18. The diagnostic kit of claim 17, wherein the antibody or antibodies are polyclonal antibodies, monoclonal antibodies or fragments of polyclonal or monoclonal antibodies.

19. The method of claim 17 wherein cholinesterase is distinguished and measured based upon eserine sensitivity.

20. A method of diagnosing the extent of activation of the pain sensing neurological pathway in a patient comprising:
   i) determining the amount of a pain marker in a biological sample obtained from said patient;
   ii) comparing the amount of the pain marker in said sample to at least one pre-determined pain marker amount;
   iii) assigning a pain status to the patient based upon the comparison.

21. A method for determining the efficacy of a treatment for pain comprising:
   i) determining the amount of a pain marker in a first biological sample obtained from said patient;
   ii) administering the treatment to said patient;
   iii) determining the amount of a pain marker in a second biological sample obtained from said treated patient; and
   iv) comparing the amount of the pain marker in the first and second biological samples.

22. A diagnostic kit for determining the level of activation of the pain sensing neurological pathway in a patient comprising at least one agent that reacts with cholinesterase in a biological sample obtained from a patient wherein the amount of cholinesterase in the sample is then compared with an amount of cholinesterase known to be indicative of activation of the pain sensing neurological pathway.

23. A method of diagnosing the extent of activation of the pain sensing neurological pathway in a patient comprising:
   i) determining the amounts of at least two pain markers in a biological sample obtained from said patient;
   ii) comparing the amounts of the at least two pain marker in said sample to a pre-determined amount of each pain marker
   iii) assigning a pain status to the patient based upon the comparison.

* * * * *